US012596125B2

(12) United States Patent
Abou et al.

(10) Patent No.: US 12,596,125 B2
(45) Date of Patent: Apr. 7, 2026

(54) NANO-RHEOLOGICAL BIOMARKERS FOR EARLY AND IMPROVED FOLLOW-UP OF PATHOLOGIES ASSOCIATED TO RBC DEFORMABILITY ALTERATION

(71) Applicants: ALCEDIAG, Peynier (FR); CENTRE NATIONAL DE LA RECHERCHE SCIENTIFIQUE (CNRS), Paris (FR); UNIVERSITE PARIS CITE, Paris (FR)

(72) Inventors: Bérengère Abou, Paris (FR); Franck Molina, Les Matelles (FR); Thomas Podgorski, Allevard (FR)

(73) Assignees: ALCEDIAG, Peynier (FR); CENTRE NATIONAL DE LA RECHERCHE SCIENTIFIQUE (CNRS), Paris (FR); UNIVERSITÉ PARIS CITÉ, Paris (FR)

( * ) Notice: Subject to any disclaimer, the term of this patent is extended or adjusted under 35 U.S.C. 154(b) by 857 days.

(21) Appl. No.: 17/618,731

(22) PCT Filed: Jun. 15, 2020

(86) PCT No.: PCT/EP2020/066524
§ 371 (c)(1),
(2) Date: Dec. 13, 2021

(87) PCT Pub. No.: WO2020/249823
PCT Pub. Date: Dec. 17, 2020

(65) Prior Publication Data
US 2022/0299533 A1 Sep. 22, 2022

(30) Foreign Application Priority Data

Jun. 14, 2019 (EP) ..................................... 19180316

(51) Int. Cl.
*G01N 33/80* (2006.01)
*G01N 15/14* (2024.01)
(Continued)

(52) U.S. Cl.
CPC ......... *G01N 33/80* (2013.01); *G01N 15/1434* (2013.01); *G01N 33/582* (2013.01); *G01N 2015/012* (2024.01); *G01N 2800/22* (2013.01)

(58) Field of Classification Search
CPC .. G01N 33/80; G01N 15/1434; G01N 33/582; G01N 2015/012; G01N 2800/22
See application file for complete search history.

(56) References Cited

U.S. PATENT DOCUMENTS

2009/0053749 A1 2/2009 Manalis et al.

FOREIGN PATENT DOCUMENTS

WO 02086472 A1 10/2002
WO 2011109762 A1 9/2011

OTHER PUBLICATIONS

Molecular rotors-fluorescent biosensors for viscosity and flow Mark A Haidekker and Emmanuel A Theodorakis Org. Biomol. Chem., 2007, 5, 1669-1678 (Year: 2007).*

(Continued)

*Primary Examiner* — Lyle Alexander
*Assistant Examiner* — Dwan A Gerido
(74) *Attorney, Agent, or Firm* — Leason Ellis LLP

(57) ABSTRACT

The present invention is directed to a method to detect in a blood sample whether the red blood cells (RBCs) contained in said blood sample present or not an alteration of their deformability by using molecular rotor (MR) able to penetrate RBCs cell membrane. The invention also relates to diagnostic methods of RBC related pathologies associated to the modification of the distribution of the viscosity, rigidity or deformability of RBCs by detection and measurement of (Continued)

Figures 1A, 1B:
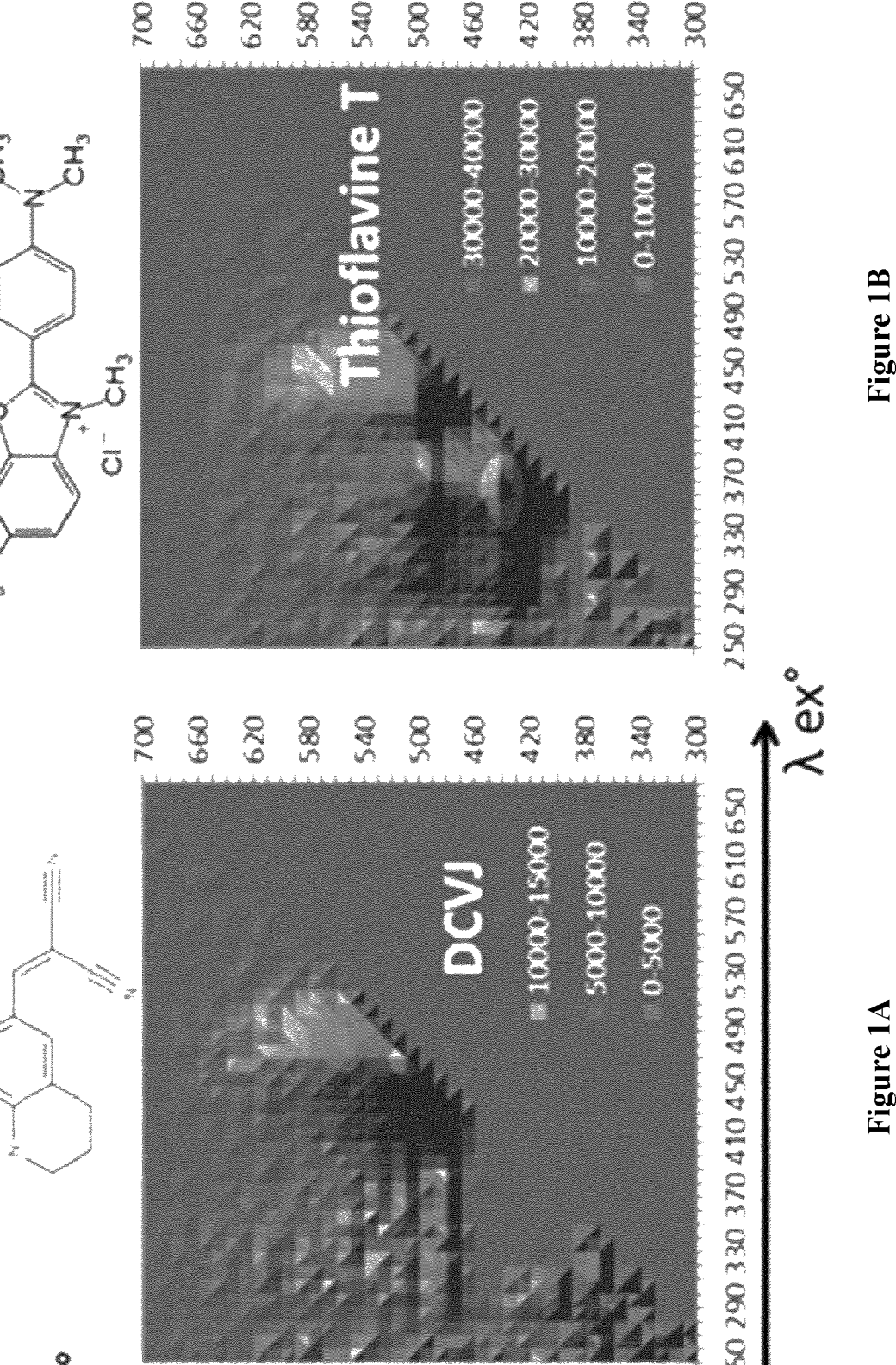

the RBCs fluorescence intensity image intensity implementing optical methods. Finally, the present invention is directed to the use of MRs for testing the deformability of red blood cells (RBCs) in a blood sample and kit comprising MR and red blood cells (RBCs) control.

10 Claims, 32 Drawing Sheets

(51) Int. Cl.
G01N 15/1434 (2024.01)
G01N 33/58 (2006.01)
*G01N 15/01* (2024.01)

(56) References Cited

OTHER PUBLICATIONS

Haidekker et al., "Molecular rotors—Fluorescent biosensors for viscosity and flow", Org. Biomol. Chem., vol. 5, No. 11, Jul. 2007, pp. 1669-1678.

Haidekker et al., "Dyes with Segmental Mobility: Molecular Rotors", Fluorescent Methods to Study Biological Membranes, Jul. 2010, vol. 8, pp. 267-308, Springer Berlin Heidelberg, Berlin, Heidelberg.

Haidekker et al. "Environment-sensitive behavior of fluorescent molecular rotors", Journal of Biological Engineering, 2010; 14 pages.

International Search Report mailed Sep. 18, 2020 for the corresponding PCT International Patent Application No. PCT/EP2020/066524 (4 pages).

* cited by examiner

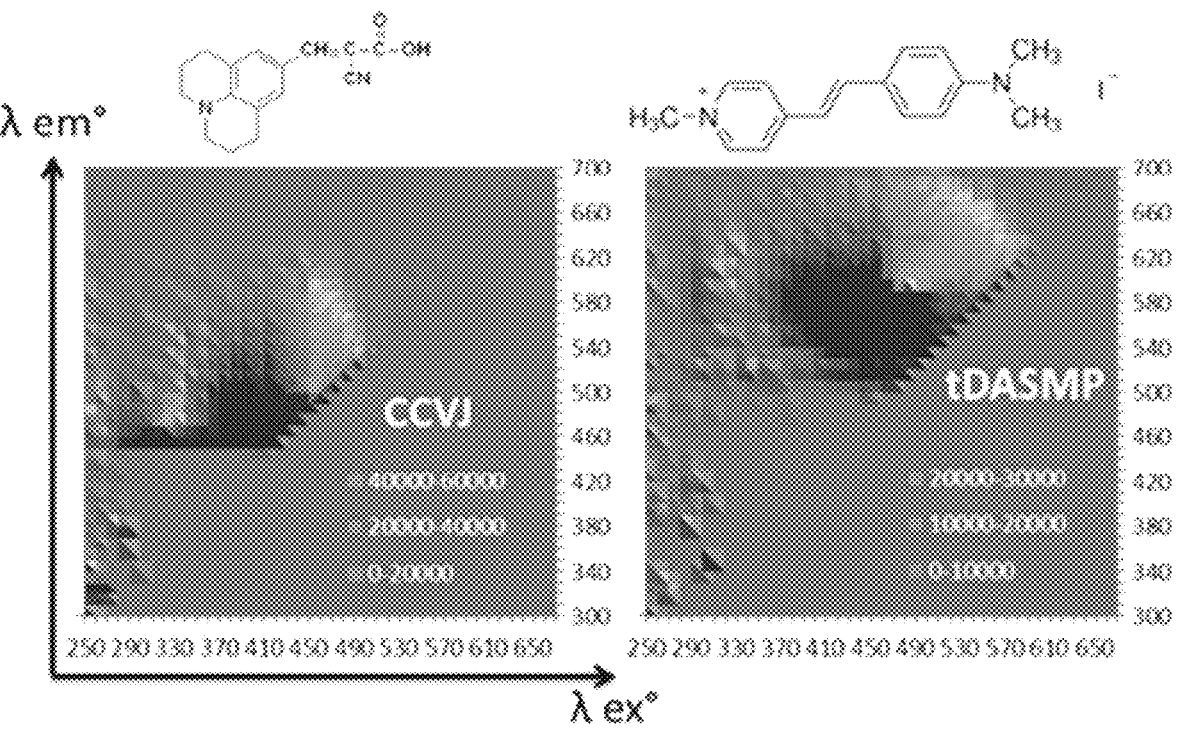
Figure 1C                    Figure 1D

NANO-RHEOLOGICAL BIOMARKERS FOR EARLY AND IMPROVED FOLLOW-UP OF PATHOLOGIES ASSOCIATED TO RBC DEFORMABILITY ALTERATION

CROSS-REFERENCE TO RELATED PATENT APPLICATIONS

This application is a U.S. National Stage Application under 35 U.S.C. § 371 of International Patent Application No. PCT/EP2020/066524 filed Jun. 15, 2020, which claims the benefit of priority of European Patent Application No. 19180316.2 filed Jun. 14, 2019, both of which are incorporated by reference in their entireties. The International Application was published on Dec. 17, 2020, as International Publication No. WO 2020/249823 A1.

The present invention is directed to a method to detect in a blood sample whether the red blood cells (RBCs) contained in said blood sample present or not an alteration of their deformability by using molecular rotor (MR) able to penetrate RBCs cell membrane. The invention also relates to diagnostic methods of pathologies associated to the modification of the distribution of the viscosity, rigidity or deformability of RBCs within a blood sample by detection and measurement of the RBCs fluorescence intensity image implementing optical microdetection methods. The present invention is also directed to the use of MRs for testing the deformability of red blood cells (RBCs) in a blood sample and kit comprising MR and red blood cells (RBCs) control.

Sickle cell anemia, or drepanocytosis, is a widespread congenital disease resulting in an abnormal form of haemoglobin (HbS). It involves a mutated β-globin gene leading to the polymerization of HbS and sickle shape of red blood cells (RBCs) under condition of low oxygen tension. It affects a worldwide annual number of 300,000 new-borns [Piel (2017)] and a total of 13,000 people in France. Besides chronic anaemia and increased sensitivity to infections, the disease leads to degenerative organ complications at young age. Although life expectancy has progressed due to better knowledge of the disease and recommendations by patients, medical follow-up and background therapy, vital risk persists and life quality is highly impacted [Habibi (2015)].

Painful vaso-occlusive crisis is the most frequent reason for seeking healthcare and is often unpredictable. The only existing curative therapy is hematopoietic stem cell allograft, which has limited indications due to its toxicity and the absence of donors other than family members. Long term therapy through hydroxycarbamide treatment, to reduce or delay organ complications, has a limited efficiency and does not prevent severe complications (acute chest syndrome, neurological stroke) and organ degradation. Concerning short term treatment, vaso-occlusive crises are managed at a symptomatic level through transfusions. However, no diagnostic test provides a reliable appreciation of the crisis risk in case of sine materia moderate pain or apparently stable clinical state.

Usual haematological test such as HbS dosage are insufficient for satisfying clinical management.

Drepanocytosis leads to rheological modifications of blood through alterations of the deformability of red blood cells, as is the case of many pathologies (atherosclerosis, diabetes, malaria or Alzheimer). Besides macroscopic blood viscosity, these modifications condition the flow of RBCs through capillaries and vaso-occlusive events, and suggest that RBC deformability is a key hemo-rheological parameter for diagnostics [Banerjee (1998), Du (2015)]. As for sickle cell disease, the RBCs stiffening during their de-oxygenation is directly related to HbS level [Barabino (2010)], which is only measured on average in the blood sample. This global marker, associated to other hematological and clinical parameters, does not provide reliable vaso-occlusive risk estimation.

It will be desirable to take into account the distribution of RBC deformability in a blood sample, as large dispersion of RBC properties may be hidden behind average indicators and be a determining factor of the occlusive risk.

Detailed statistical information on this distribution for diagnosis purposes requires an intracellular measurement technique easy to implement in a clinical framework.

Several techniques have been proposed to characterize RBC deformability. Ektacytometry, developed in the 1980's [Bessis (1980)], is based on light diffraction through a blood sample in a shear flow, to measure a RBC elongation index. The results interpretation is often difficult [Rabai (2014)] and recent papers underline the lack of clear link between ektacytometry and the quality of perfusion in capillaries [Sosa (2014)]. Moreover, results are sensitive to the methodology variability [Renoux (2015)]. Finally, ektacytometry inherently provides an indication of the RBC average deformability in the sample. Despite recent attempts to estimate the deformability dispersion by analysing the shape of the diffraction figure [Nikitin (2015)], results remain approximate and difficult to interpret, in addition to the fact that the technique requires expensive equipment.

Recently, microfluidic techniques analysing the RBC deformation in microfluidic flows such as contraction-expansion flows have been proposed to characterize deformability at the individual cell level [Guo (2014), Kim (2015)]. Although they partly answer the question of the dispersion of properties in a sample, they require heavy image processing and shape analysis giving indirect information that relies on theoretical modelling. Other techniques which consist in studying occlusion of microfluidic channels upon blood deoxygenation also provide interesting information on pathological blood properties and the occlusive risk but again require complex devices and protocols difficult to implement in a clinical practice [Li (2017)].

To date, no test has been specifically disclosed or approved by drug regulatory agencies, as an effective and easy test for identifying patient exhibiting rheological modifications of blood through alterations of the deformability of red blood cells at the single cell level, and/or for predicting vaso-occlusive risk for a patient associated to these alterations.

Thus there is a need to provide with in vitro test, which can determine with accuracy and with discriminate power the risk for a patient to present or to develop a pathology associated to the modification of the deformability of a fraction of RBCs, such as drepanocytosis, atherosclerosis, diabetes, malaria or Alzheimer.

The estimation or determination of the modification or the distribution of RBC deformability in a blood sample could be used to monitor the status of a patient and will open new possibilities to evaluate primary or severe vaso-occlusive risks.

This is the object of the present invention.

Remarkably, the inventors have demonstrated for the first time that nano-rheology technique based on molecular rotors (MRs) can be used for evaluating rheological modifications of blood through alterations of the deformability of red blood cells, and for estimating the dispersion and/or the distribution of RBC deformability in a blood sample.

MRs are fluorescent sensors with a quantum yield related to the transition probability between different molecular conformations, with a strong sensitivity to the environment. They were shown to be sensitive to the local micro-viscosity and can penetrate cell membranes due to their nanometric size, provided molecular interaction permit it. Molecular rotors are a group of fluorescent molecules that form twisted intra-molecular charge transfer (TICT) states upon photo-excitation. When intra-molecular twisting occurs, the molecular rotor returns to the ground state either by emission of a red-shifted emission band or by non-radiative relaxation. The emission properties strongly depend on the medium, its viscosity being the primary determinant of the fluorescent quantum yield from the planar (non-twisted) conformation [Haidekker (2010a)]. Indeed, constraining molecular motions, e.g. by increasing viscosity, favors the planar conformation over the twisted one and therefore leads to an increase of the quantum yield with viscosity. It has been shown, in a wide range of pure fluids, that the quantum yield of molecular rotors is related to viscosity η by a power law (depending on the fluorophore and other physico-chemical characteristics) [Haidekker (2010b)]:

$$\log \phi = C + b \log \eta$$

where C and b are solvent- and dye-dependent constants (Förster-Hoffmann equation).

The MRs as defined earlier are molecule having electron donor and electron acceptor separated par a rotational axis and for which a wavelength emission varies with local rheological modifications. For examples, the following MRs can be cited:

Dicyanovinyl-Julolidine (DCVJ),
Carboxycyanovinyl-Julolidine (CCVJ),
Thioflavine T (Tht), and
trans-4-[4-(Dimethylamino)styril]-1-methylpyridinium (tDASMP).

Other MRs according to our MR definition may be used for specific optical readout (for instance wavelength) if needed.

A particular difficulty in the case of red blood cells lies in the absorption and fluorescence spectra of haemoglobin, which are quite rich and wide. After choosing an appropriate molecule with interesting spectral properties, quantification of possible interactions with RBC components (haemoglobin, membrane constituents) can be investigated.

Another particular difficulty is that the MR has to be soluble, preferably in aqueous solvent or in non-aqueous solvent which does not induce the RBC lysis.

After choosing an appropriate molecule with interesting spectral properties, quantification of possible interactions with RBC components (haemoglobin, membrane constituents) can be investigated.

Are preferred, MRs selected from the group of MRs having an excitation peak which does not interfere or overlap with the excitation/emission fluorescence spectra of RBC and haemoglobin, preferably which further penetrate into the RBC and are soluble in aqueous solvent or in non aqueous solvent which does not induce the RBC lysis.

Preferably excitation peak is above 450 nm and emission peak is above 550 nm.

Surprisingly, the inventors have found that MRs can be used in the method of the present invention as disclosed before, particularly:

trans-4-[4-(Dimethylamino)styril]-1-methylpyridinium (tDASMP) or,
Chemically modified versions of tDASMP with the attachment of different targeting or recognition elements.

tDASMP is the most preferred MR.

For the first time, the inventors have shown that a MR can be used as an effective and easy test for the intra-cellular evaluation of RBC mechanical properties, at the single cell level, test based on MR fluorescence modifications in relation to local rheological changes, due to the alteration of the deformability of red blood cells, especially in the framework of haematological tests, diagnostics and clinical follow-up.

In a first aspect, the present invention is directed to a method to detect in a blood sample whether the red blood cells (RBCs) contained in said blood sample present or not an alteration of their deformability, said method comprising the steps of:

a) mixing the blood sample containing RBCs to be tested with a molecular rotor (MR) able to penetrate RBCs through the cell membrane;

b) quantifying the level of fluorescent signal emitted by the molecular rotor or/and analysing the distribution of RBC fluorescence level in the sample; and c) comparing the RBCs fluorescence level and/or the distribution of RBC fluorescence level obtained in step b) with those obtained for control blood sample containing RBCs, a notable increase of the emitted fluorescent signal and/or notable modification of the distribution of RBC fluorescence level compared to the control signal being significant of an alteration of the RBCs deformability present in the blood sample to be tested.

By the term "molecular rotor" (MR) or fluorescent molecular rotor (FMR), it is generally intended to designate a fluorescent molecule that has the ability to undergo an intramolecular twisting motion in the fluorescent excited state. This molecular rotor consists of at least three subunits, an electron donor unit, an electron acceptor unit, and an electron-rich spacer unit that is composed of a network of alternative single and double bonds (Haiddeker et al. 2010a and 2010b).

A MR can be also defined, as a molecule which comprises an electron donor and an electron acceptor directly or indirectly joined by a rotatable bond. Indirect binding of the electron donor and electron acceptor occurs when at least one other molecule or functional group lies between the donor and acceptor. The bond is said to be rotatable because under certain circumstances the bond is freer to rotate than others; for example, rotation may be hindered in a high-viscosity environment, or when the bond is in proximity to another molecule. MRs which can be used in the present invention are characterized by a charge-transfer-excited singlet state which can rapidly deactivate through internal rotation about the donor acceptor bond. When rotation is hindered, the primary deactivation pathway is radiative, and an increase in fluorescence quantum yield is observed (see WO2007041241, Brenner at al.).

Preferably, in the method of the present invention, the MR is:

trans-4-[4-(Dimethylamino)styril]-1-methylpyridinium (tDASMP) or,
Chemically modified versions of tDASMP with the attachment of different targeting or recognition elements.

More preferably, the MR is tDASMP.

In a second aspect, the invention is directed to a method to identify whether a patient presents or to identify whether a patient is at risk to develop a RBC related pathology, said RBC related pathology being associated to an alteration of RBCs deformability, said method comprising the steps of:

A) from a blood sample containing RBCs obtained from the patient to be tested, detecting by the above method of the present invention whether the RBCs present or not an alteration of their deformability; and B) the results obtained in step A) allowing to identify that said patient presents or not, or is at risk or not to develop such a RBC related pathology.

Preferably, in the method of the present invention, the MR is:

trans-4-[4-(Dimethylamino)styril]-1-methylpyridinium (tDASMP) or,

Chemically modified versions of tDASMP with the attachment of different targeting or recognition elements.

More preferably, the MR is tDASMP.

In a third aspect, the present invention also relates to a method for diagnosing a RBC related pathology or disorder associated with the presence of an alteration of the RBCs deformability in a subject, comprising:

i) mixing a blood sample containing RBCs from the subject with MR; and ii) detecting the presence or absence of an increase in the fluorescent signal of the MR, wherein an increase in the fluorescent signal indicates the presence of the pathology or disorder in the subject.

Preferably, in the method of the present invention, the MR is:

trans-4-[4-(Dimethylamino)styril]-1-methylpyridinium (tDASMP) or,

Chemically modified versions of tDASMP with the attachment of different targeting or recognition elements.

More preferably, the MR is tDASMP.

In another aspect, the invention concerns a method for diagnosing a RBC related pathology associated with an alteration of the distribution of the rigidity and/or the viscosity and/or the deformability of the RBCs in a blood sample from a subject, comprising:

i) mixing a blood sample containing RBCs from the subject with MR; and ii) determining by optical method the distribution of the rigidity and/or the viscosity and/or the deformability of the RBCs by measuring the fluorescence intensity of the image of the blood sample, visualized for example by microscopy or by microfluidic system.

In a preferred embodiment, the optical microscopy in step ii) of the method according to the present invention is a microscope coupled to a camera, preferably including an analysing software for the detection and/or the quantification of the RBCs fluorescence intensity.

Preferably, in the method of the present invention, the MR is:

trans-4-[4-(Dimethylamino)styril]-1-methylpyridinium (tDASMP) or,

Chemically modified versions of tDASMP with the attachment of different targeting or recognition elements.

More preferably, the MR is tDASMP.

In another aspect, the present invention is directed to the use of trans-4-[4-(Dimethylamino)styril]-1-methylpyridinium (tDASMP) or chemically modified versions of tDASMP with the attachment of different targeting or recognition elements, for testing the deformability of red blood cells (RBCs) in a blood sample.

Finally, the present invention is directed to a kit comprising:

trans-4-[4-(Dimethylamino)styril]-1-methylpyridinium (tDASMP) or chemically modified versions of tDASMP with the attachment of different targeting or recognition elements, and red blood cells (RBCs) control exhibiting non alteration of their deformability and/or exhibiting alteration of their deformability associated to a pathology, preferably drepanocytosis.

This will lead to establish the principle of a proof-of-concept simple and high troughputs diagnostic test that consists in diluting a small blood sample in a molecular rotor solution— by means of optimized protocols and get a distribution of RBC fluorescence levels in the sample thanks to a simplified fluorescence scan. The output will be interpreted in terms of cell rigidity distribution thanks to fundamental characterizations and calibrations, and vaso-occlusive risk through clinical studies.

The distribution of the red blood cells viscosity/rigidity/deformability will be extracted from the single measurement of the image intensity of RBCs of a blood sample, visualized for example under a microscope or by microfluidic system. The novelty of this technique lies in the fact that it gives access to the distribution of the viscosity or deformability of individual RBCs at a large scale, with a high-speed test and simple set-up. In the framework of a clinical study involving selected patient profiles, this characterization in association with clinical and other haematological parameters will form a new kind of biomarker based on more precise information than current global indicators.

In a particular preferred embodiment, in the method of the present invention, said pathology is selected from the group consisting of drepanocytosis, atherosclerosis, diabetes, malaria and Alzheimer.

Drepanocytosis is one of the most prominent RBC related pathologies associated with an alteration of the distribution of the rigidity and/or the viscosity and/or the deformability of the RBCs in a blood sample from a subject.

In yet another preferred embodiment of the method of the present invention, the solution of MR is diluted in the blood sample in step a) or i) according to a protocol described in Example 2; and in step b) or ii), the distribution of the RBCs fluorescence level is analysed and compared to a control sample in step c).

It is to be understood that both the foregoing general description and the following detailed description are exemplary and explanatory only and are not intended to limit the scope of the current teachings. In this application, the use of the singular includes the plural unless specifically stated otherwise.

Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

The following examples, the figures and the legends hereinafter have been chosen to provide those skilled in the art with a complete description in order to be able to implement and use the present invention These examples are not intended to limit the scope of what the inventor considers to be its invention, nor are they intended to show that only the experiments hereinafter were carried out.

Other characteristics and advantages of the invention will emerge in the remainder of the description with the Examples and Figures, for which the legends are given hereinbelow.

FIGURE LEGENDS AND BRIEF DESCRIPTION
OF THE FIGURES

FIG. 1A-1D: Excitation-emission matrix (EEM) of 4 rotors DCVJ (FIG. 1A), CCVJ (FIG. 1B), Tht (FIG. 1C) and, tDASMP (FIG. 1D).

Excitation wavelength in abscissa, emission in ordinates, in nanometer (nm)). The rotors are diluted in a water/glycerol solution at a concentration 15 μM. The rotor Tht exhibits two distinct excitation/emission peaks around 380/440 nm and 430/490 nm.

Figure 2A:
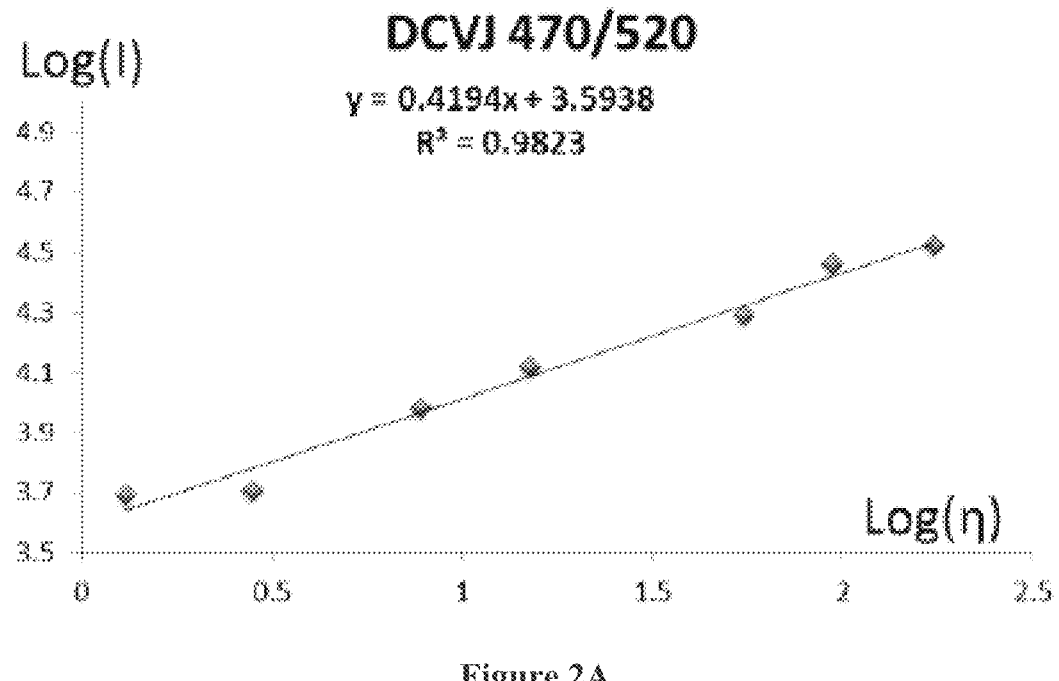
Figure 2B:
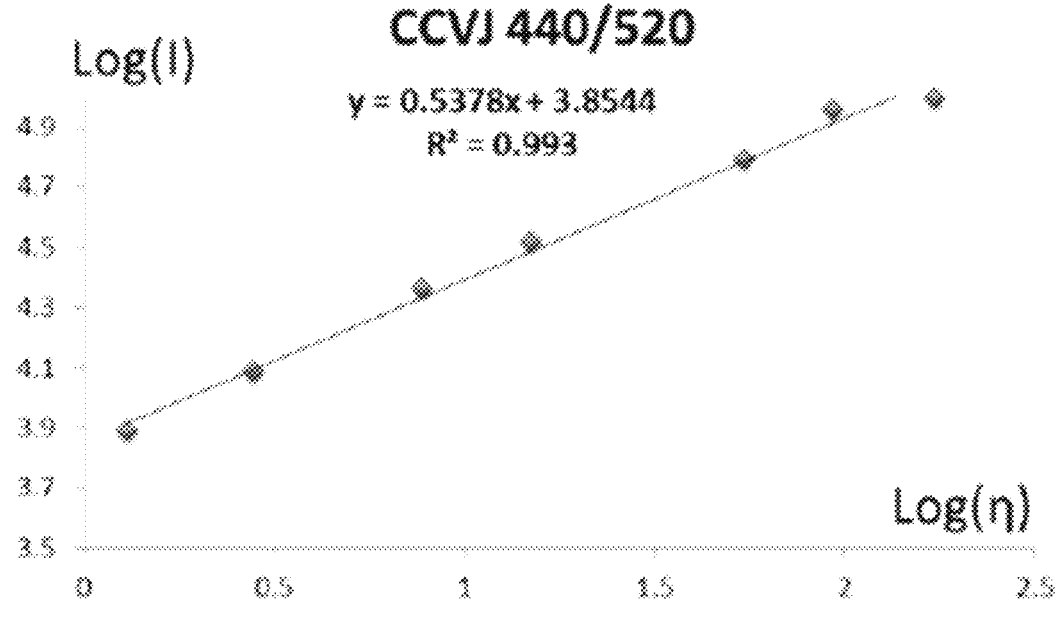
Figure 2C:
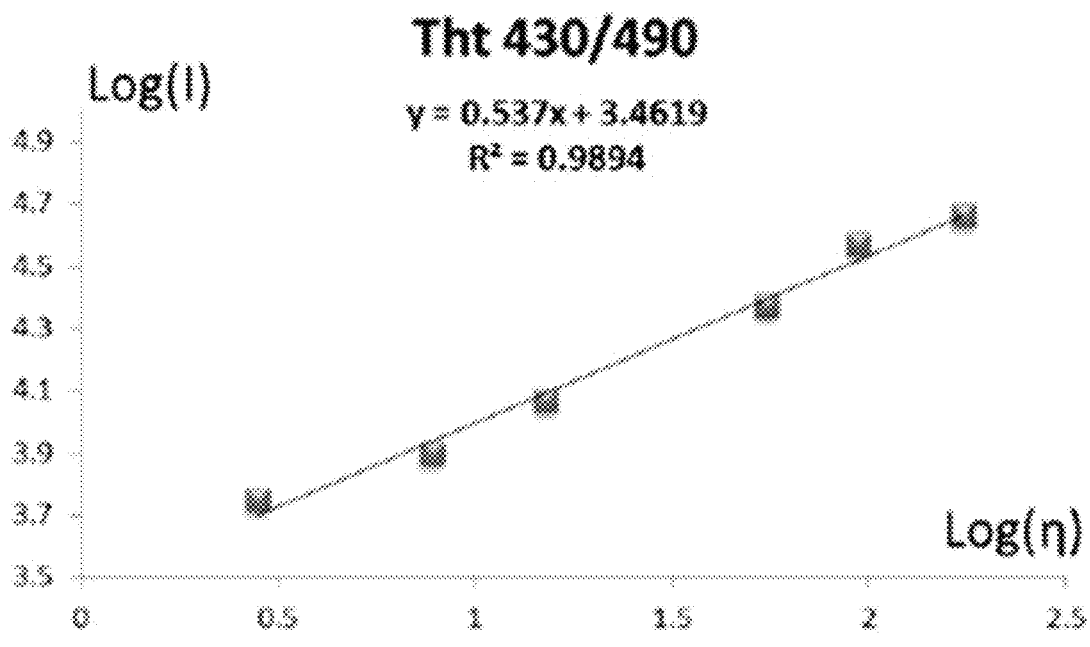
Figure 2D:
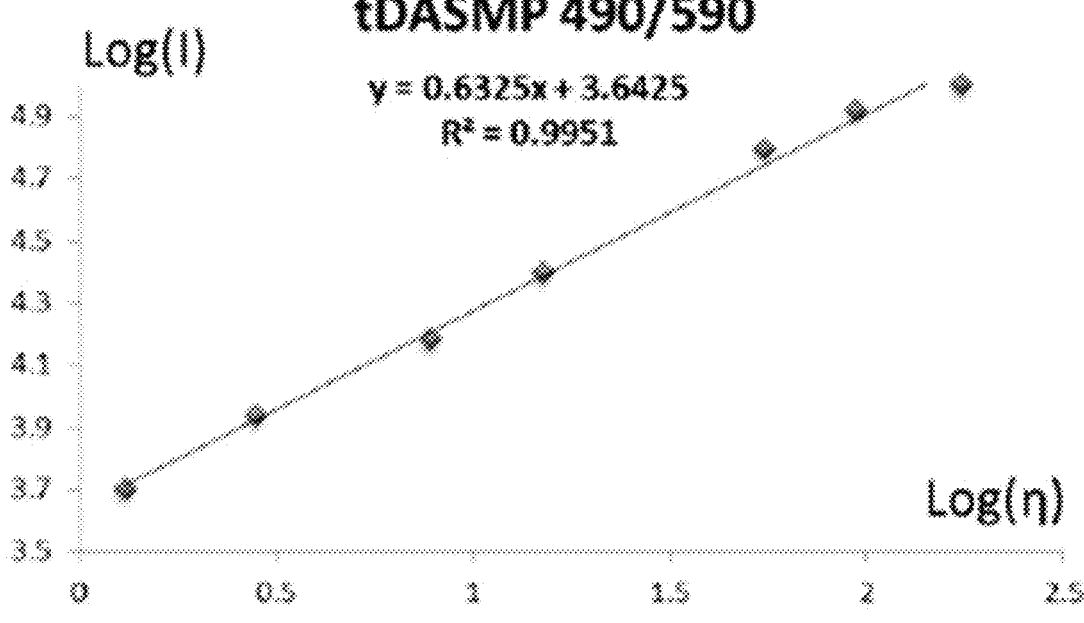

FIGS. 2A-2D: Fluorescence intensity I as a function of viscosity η (log-log plot, here y=log I and x=log η)) for the 4 investigated rotors 4 rotors DCVJ (FIG.2A), CCVJ (FIG. 2B), Tht (FIG. 2C) and tDASMP (FIG. 2D).

Viscosity η is varied in the range 1-200 mPa·s.

Each rotor follows the Förster-Hoffmann equation log I=C+b log η with specific values for b and C which are rotor and solvent dependent. For the rotor Thioflavine, the only excitation/emission peak following the Förster-Hoffmann equation is the 430/490 nm.

Figure 3A:
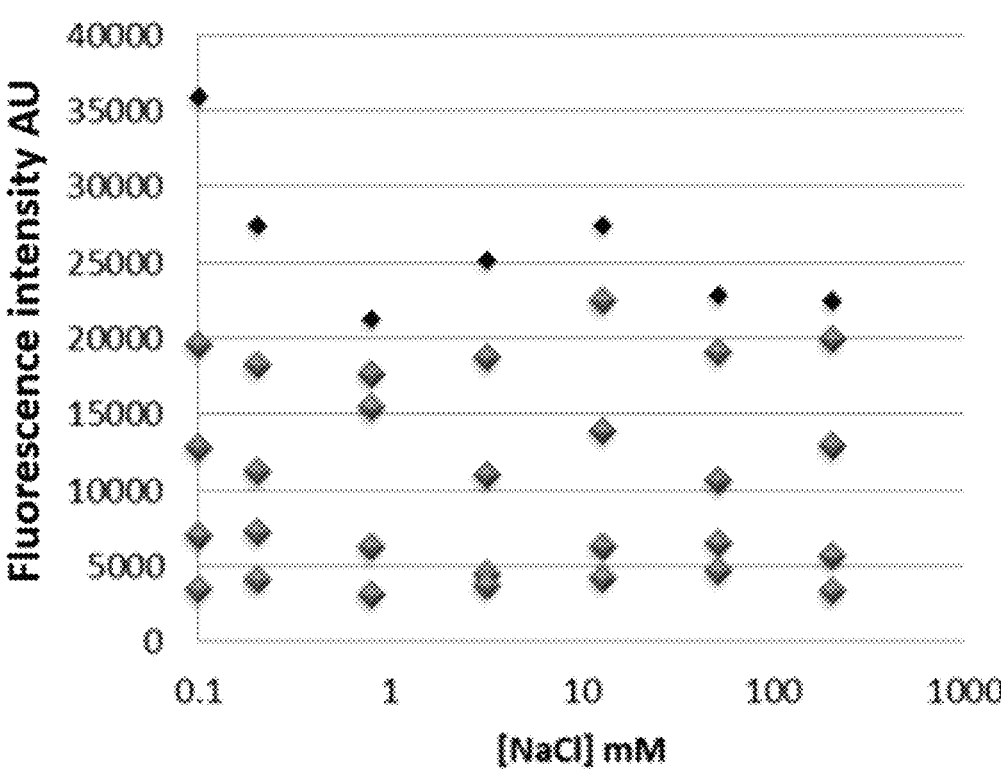
Figure 3B:
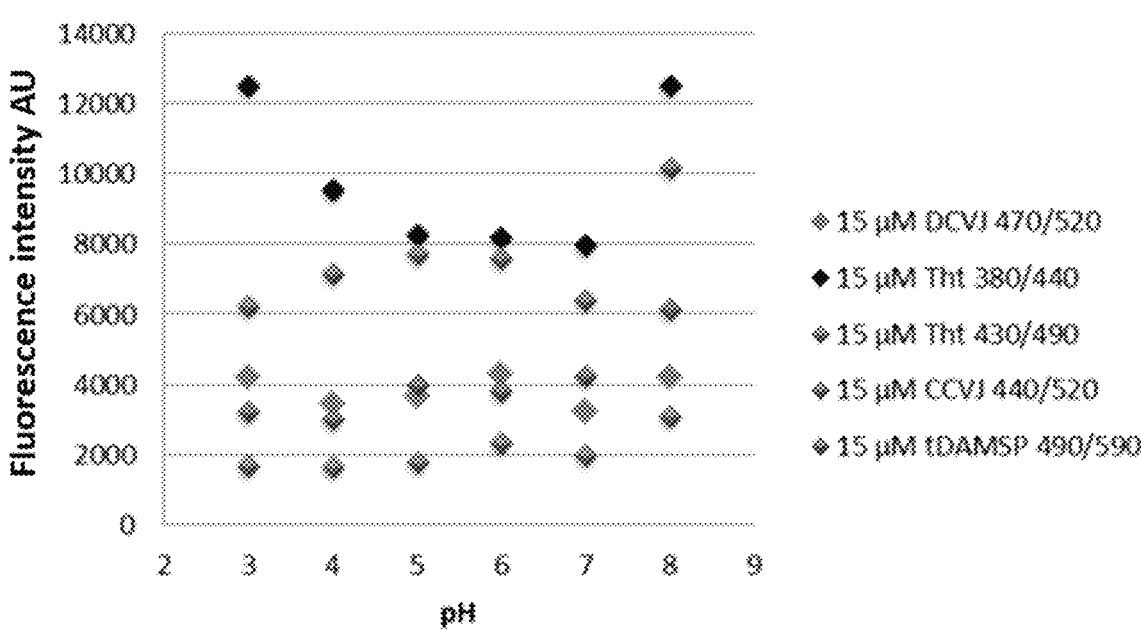
Figure 4A:
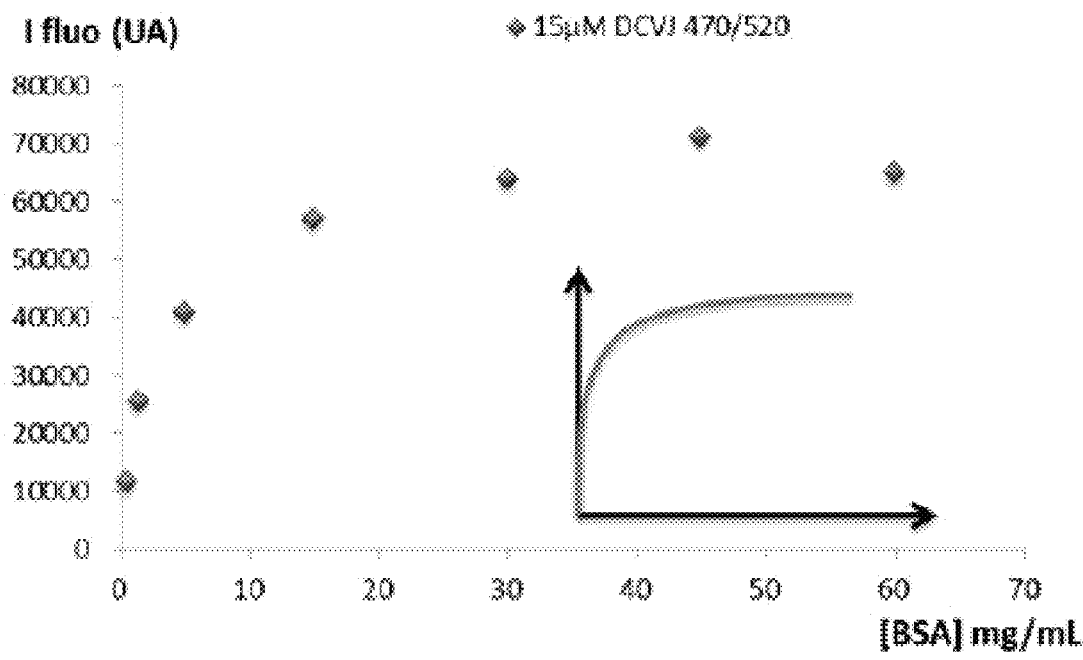
Figure 4B:
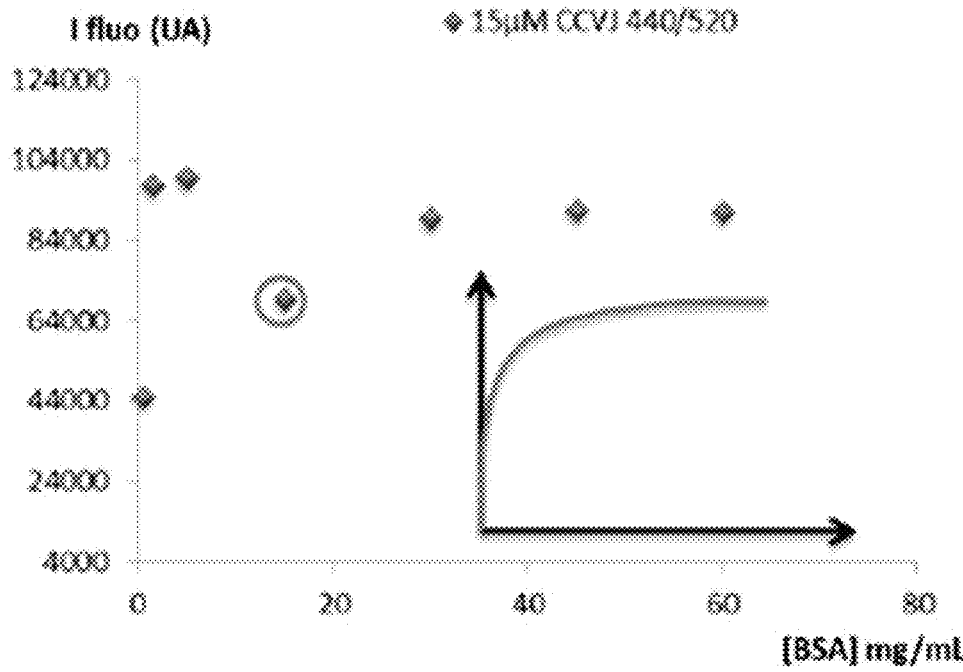
Figure 4C:
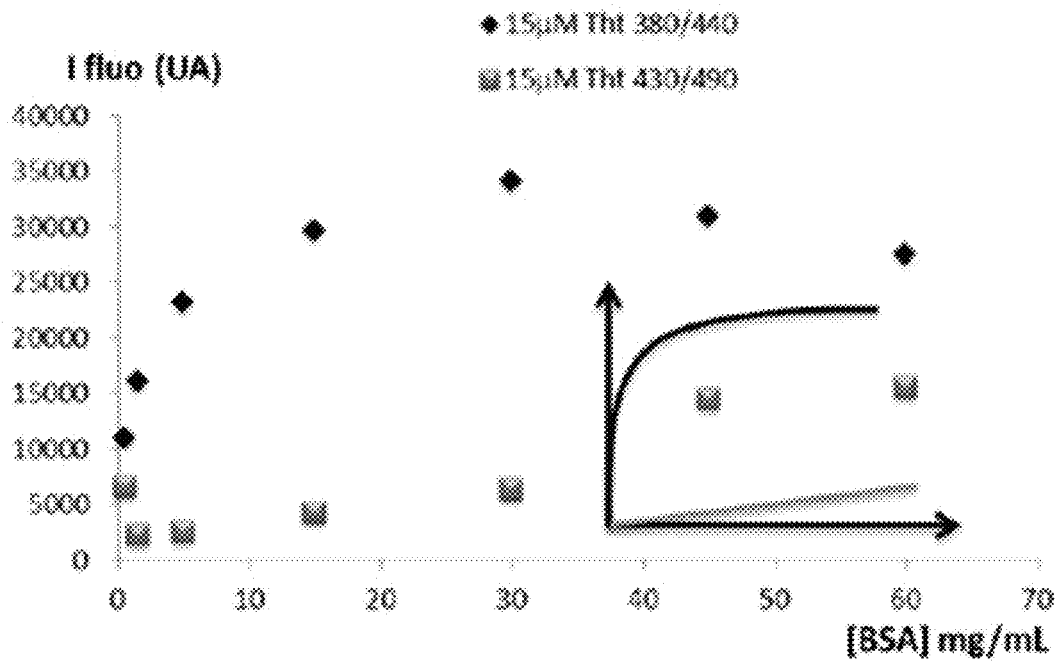
Figure 4D:
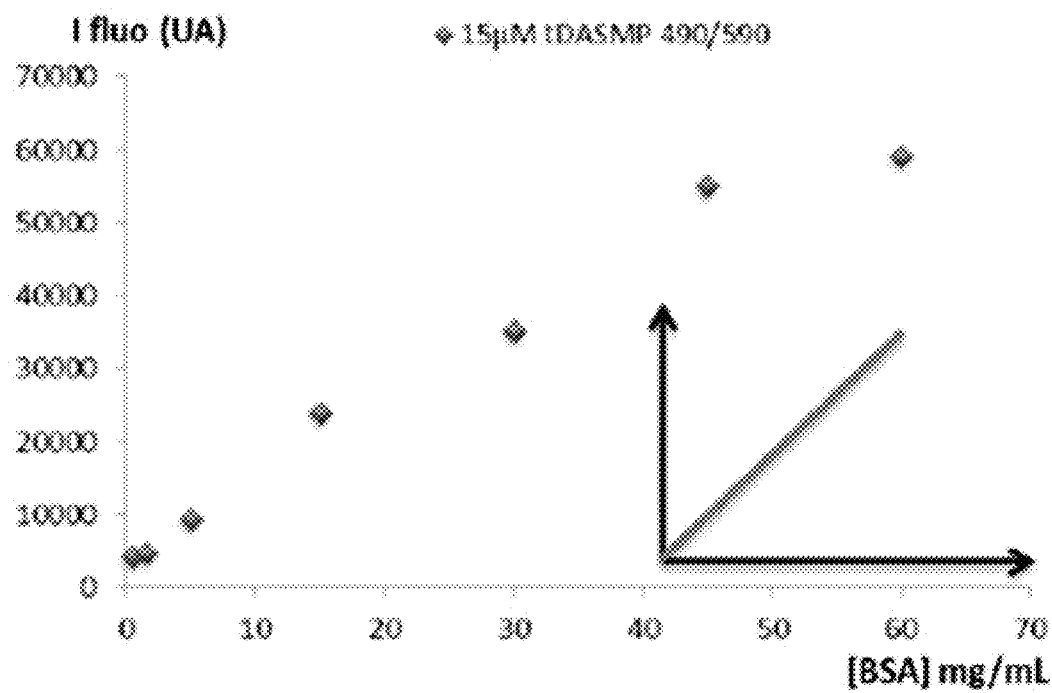
Figure 5A:
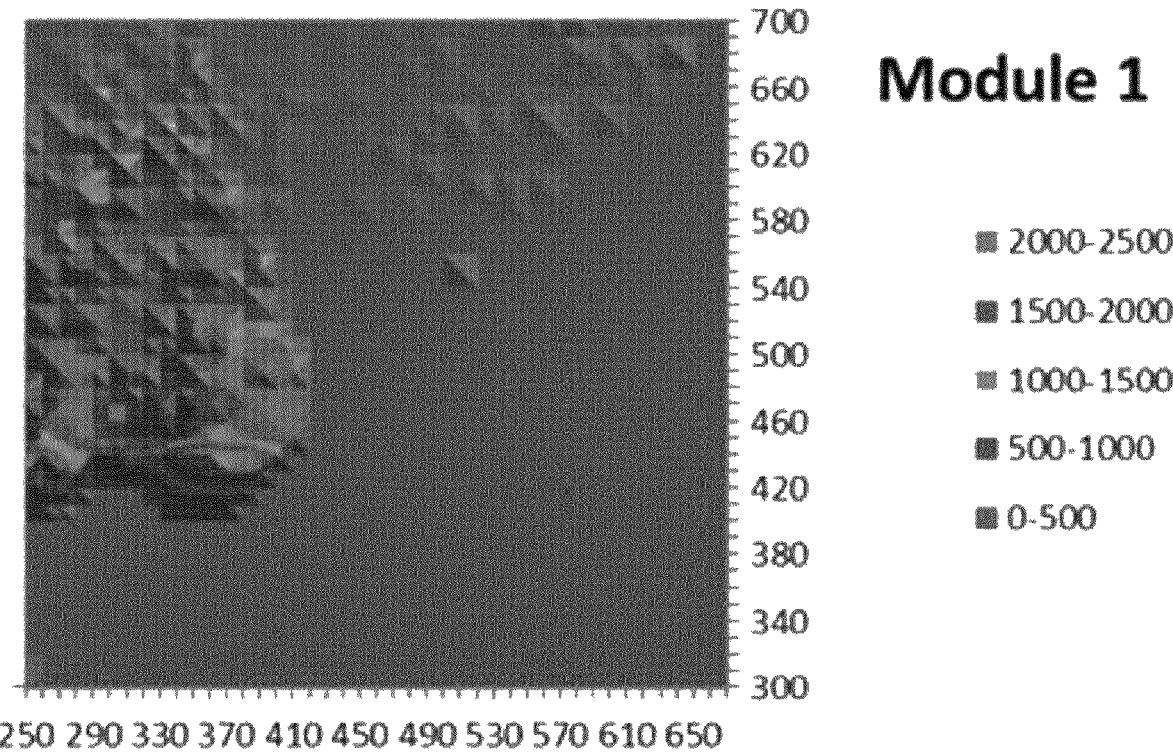
Figure 5B:
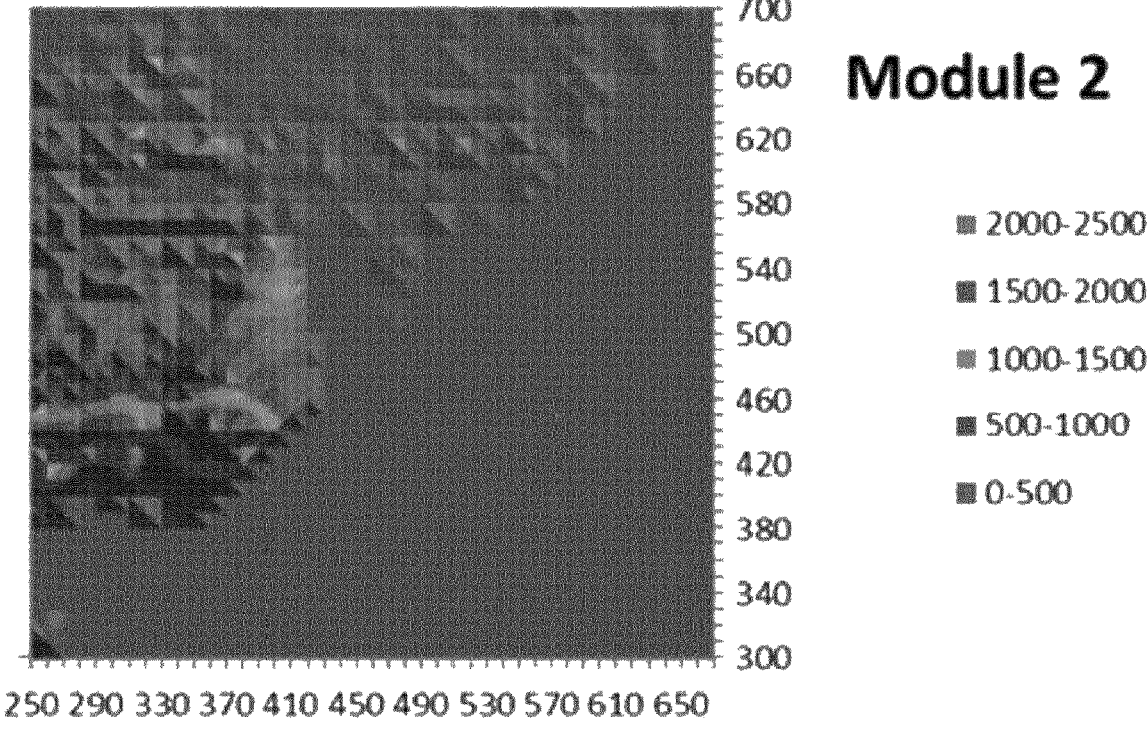
Figure 5C:
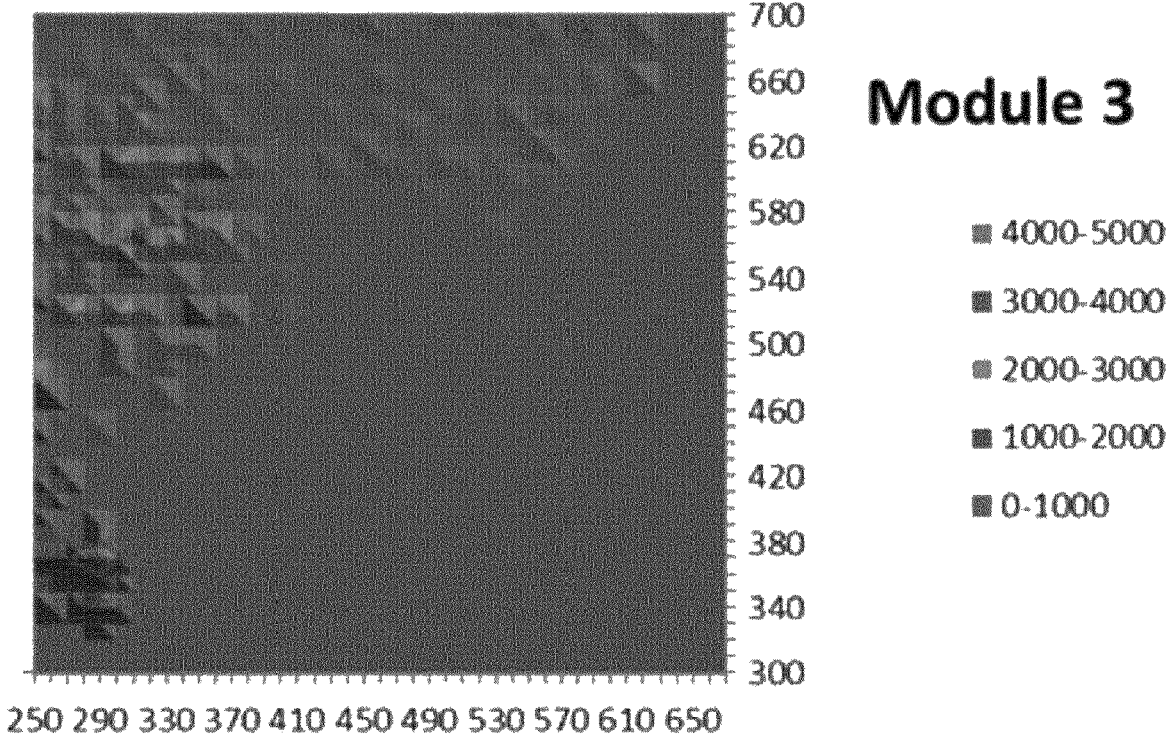
Figure 5D:
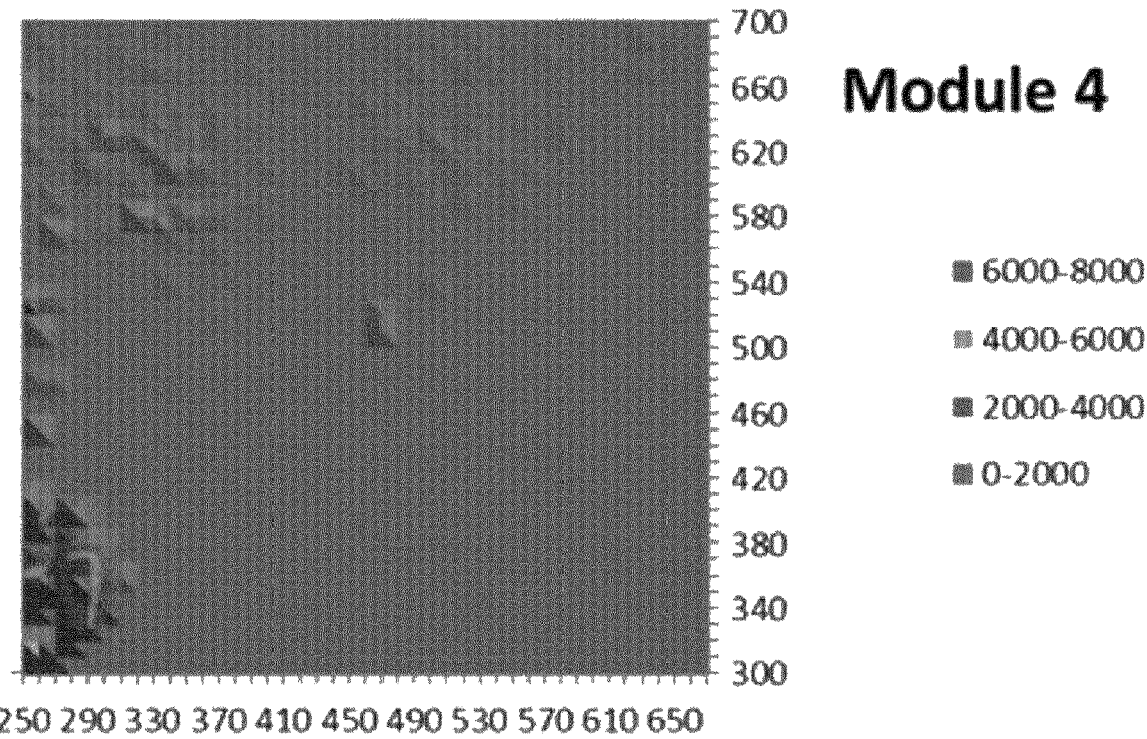

FIGS. 3A-3B: Fluorescence intensity as a function of NaCl concentration (FIG. 3A) and pH (FIG. 3B) for the 4 rotors DCVJ, CCVJ, Tht and, tDASMP. The 4 rotors investigated show no significant dependency on the parameters pH and ionic strength.

FIGS. 4A-4D: Fluorescence intensity as a function of the BSA concentration in mg/mL for the 4 rotors DCVJ (FIG. 4A), CCVJ (FIG. 4B), Tht (FIG. 4C), and, tDASMP (FIG. 4D), at constant viscosity, revealing interactions between the rotor and BSA that need to be taken into account.

FIGS. 5A-5D: Emission-Excitation Matrixes of healthy (5A) and pathological RBCs (5B), and healthy (5C) and pathological blood (5D).

Figure 6:
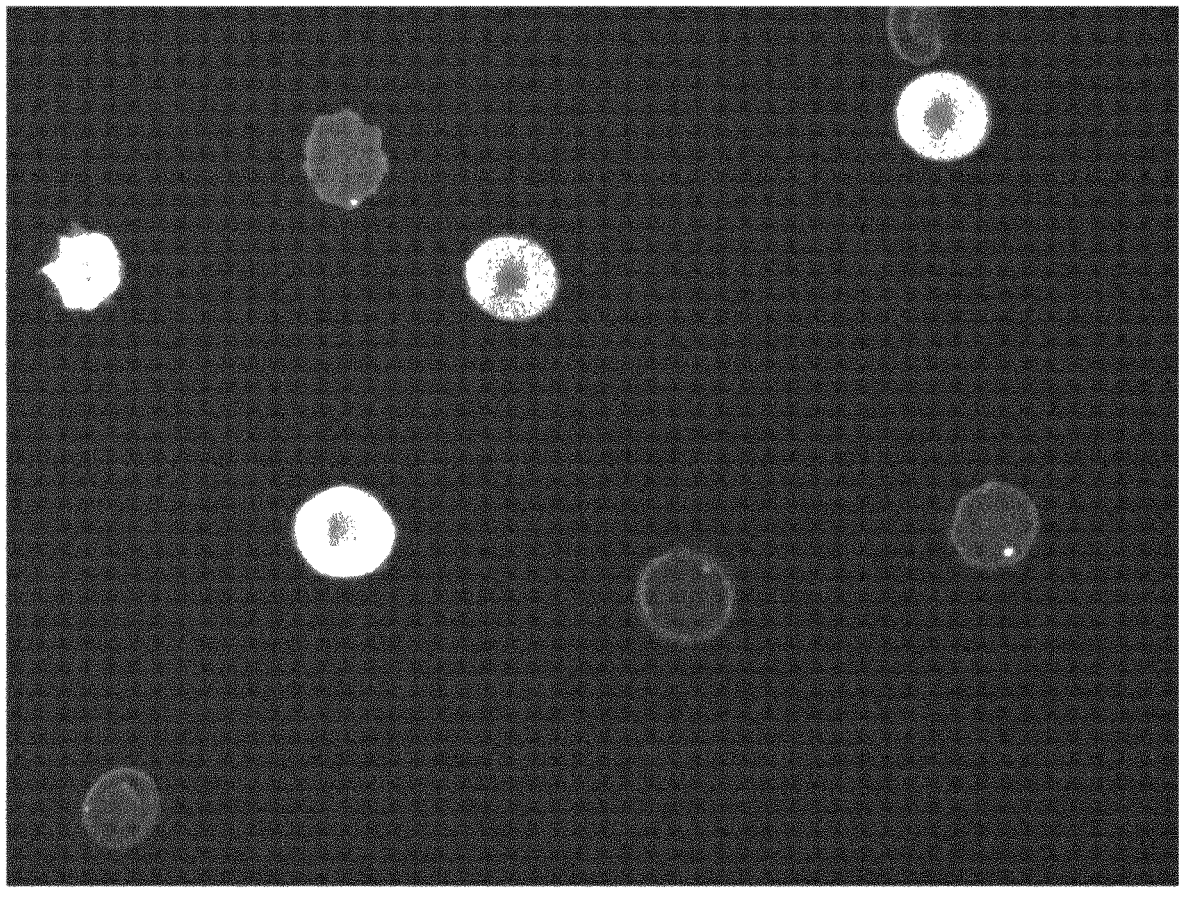

FIG. 6: Left: Suspension of healthy red blood cells and red blood cells stiffened with glutaraldehyde, in a PBS solution, using confocal microscopy (×40 objective, excitation at 488 nm, detection between 542-626 nm). The molecular rotor tDASMP was introduced into the solution according the protocol described in Example 2.

Figure 7:
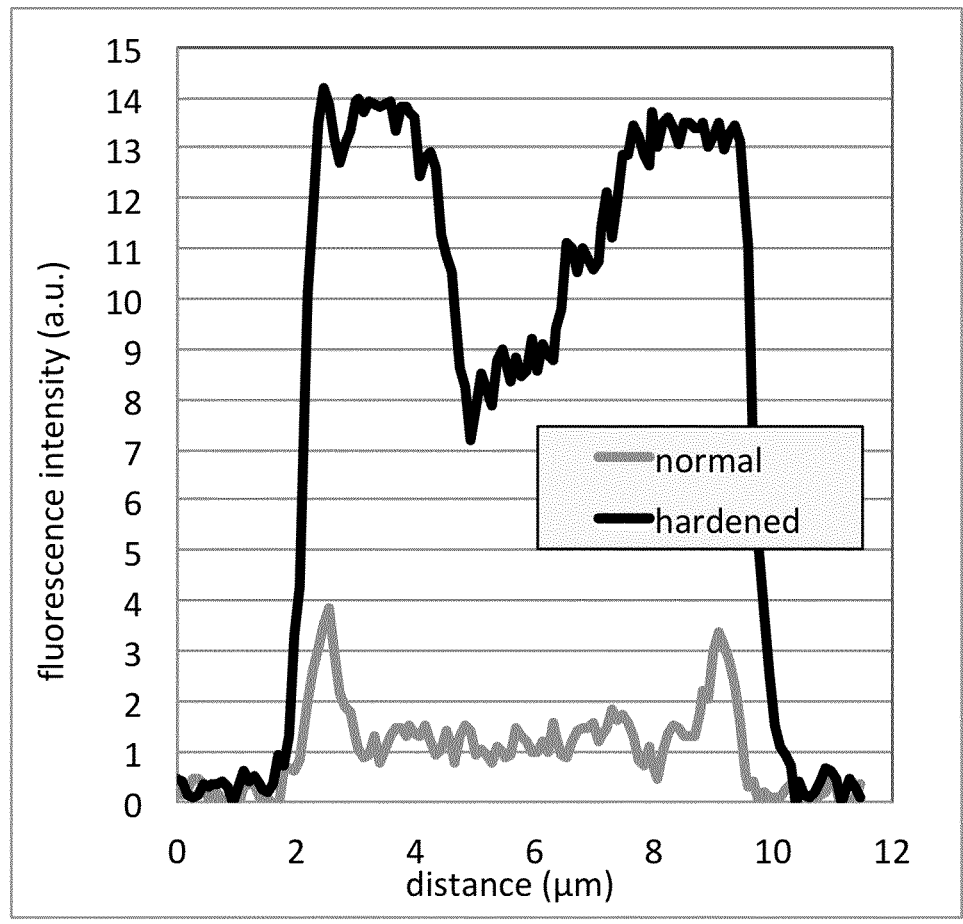

FIG. 7: Fluorescence intensity profiles along a cross-section of RBCs showing that the MR penetrates inside the cells. The fluorescence intensity here is more than 10 times higher for stiffened RBCs than for healthy ones showing the sensitivity of the MR to intracellular viscosity.

Figure 8:
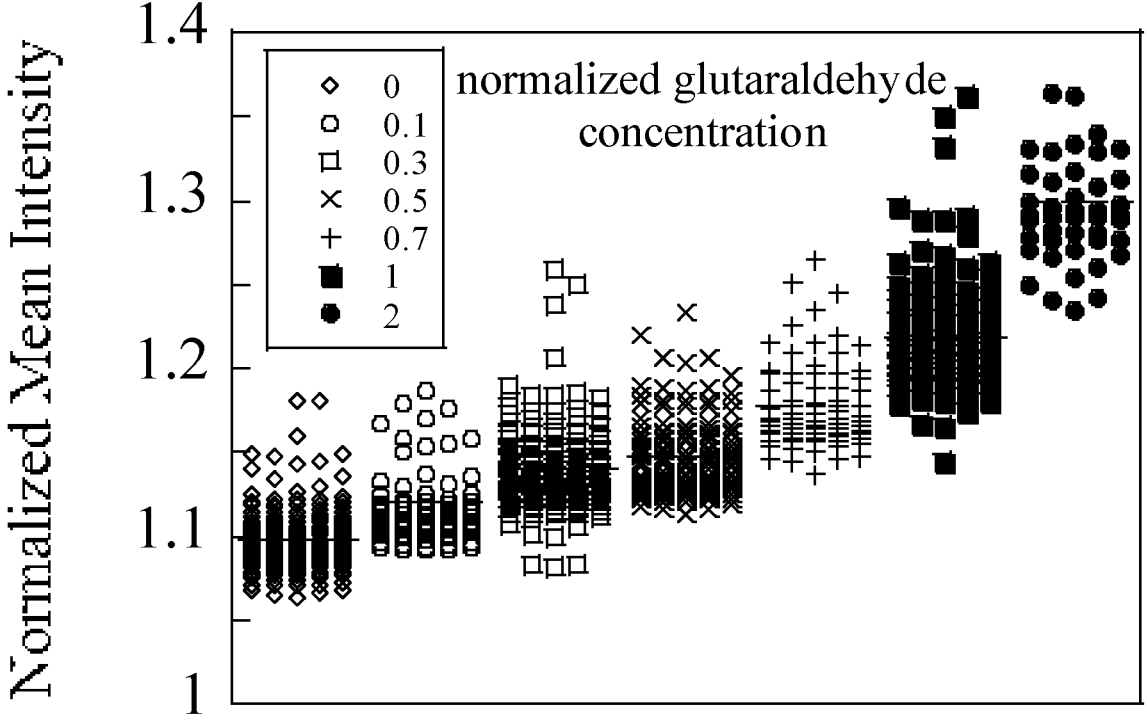
Figure 9A:
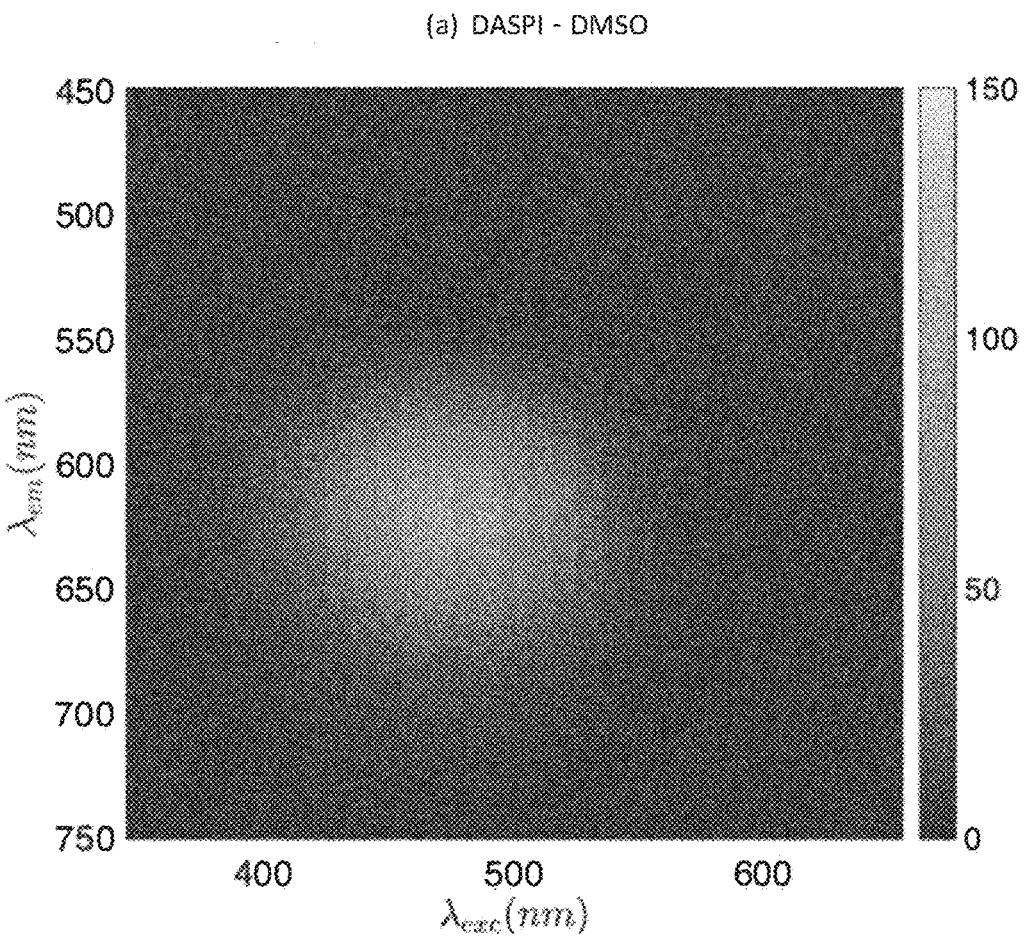
Figure 9B:
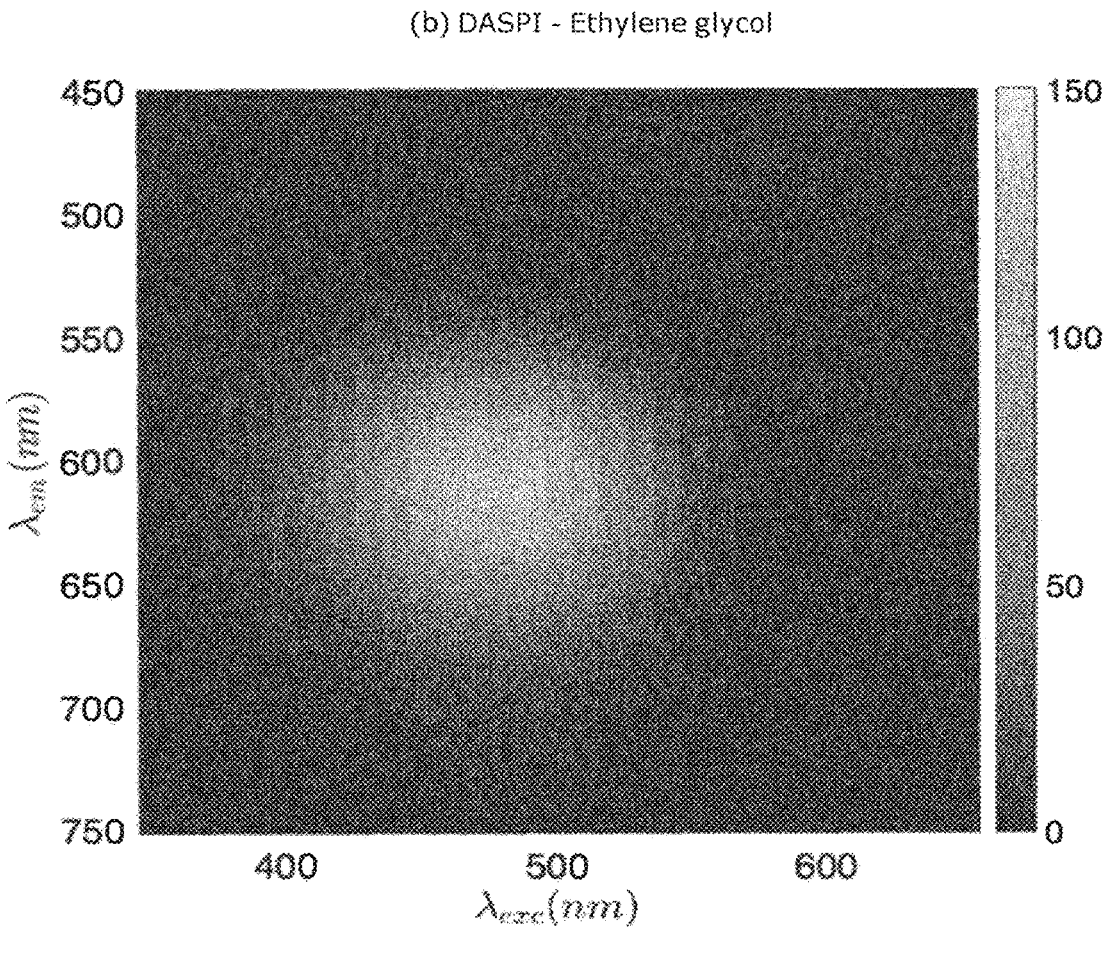
Figure 9C:
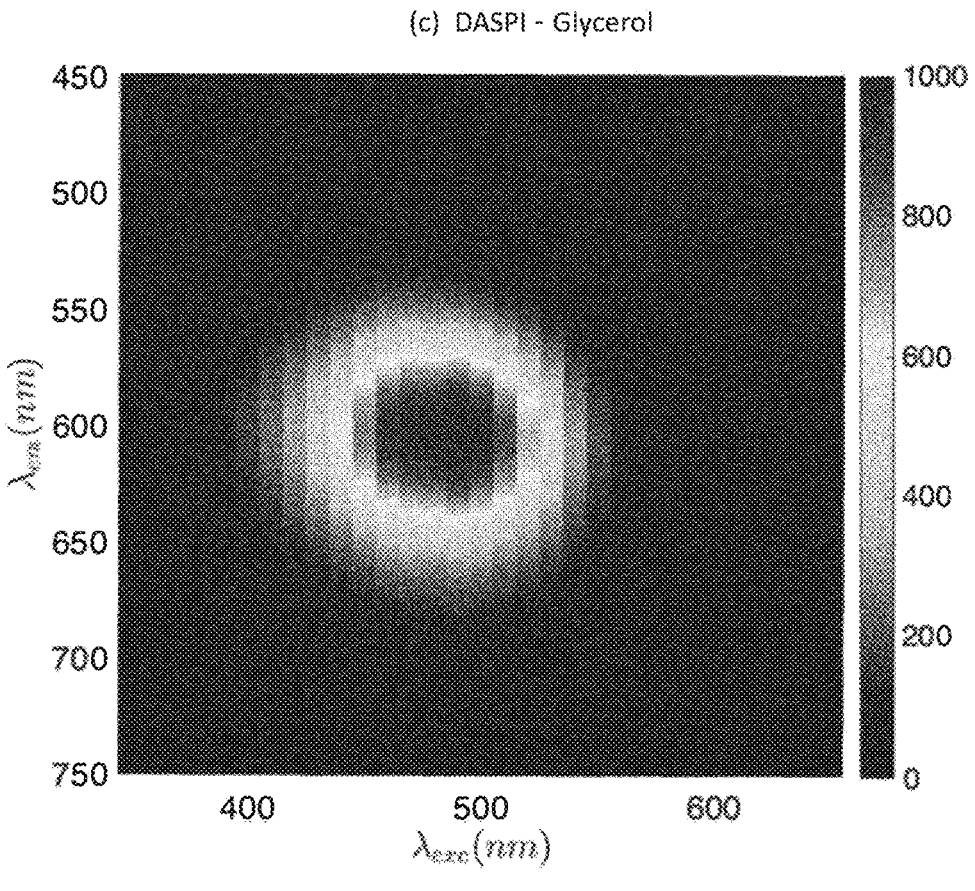
Figure 9D:
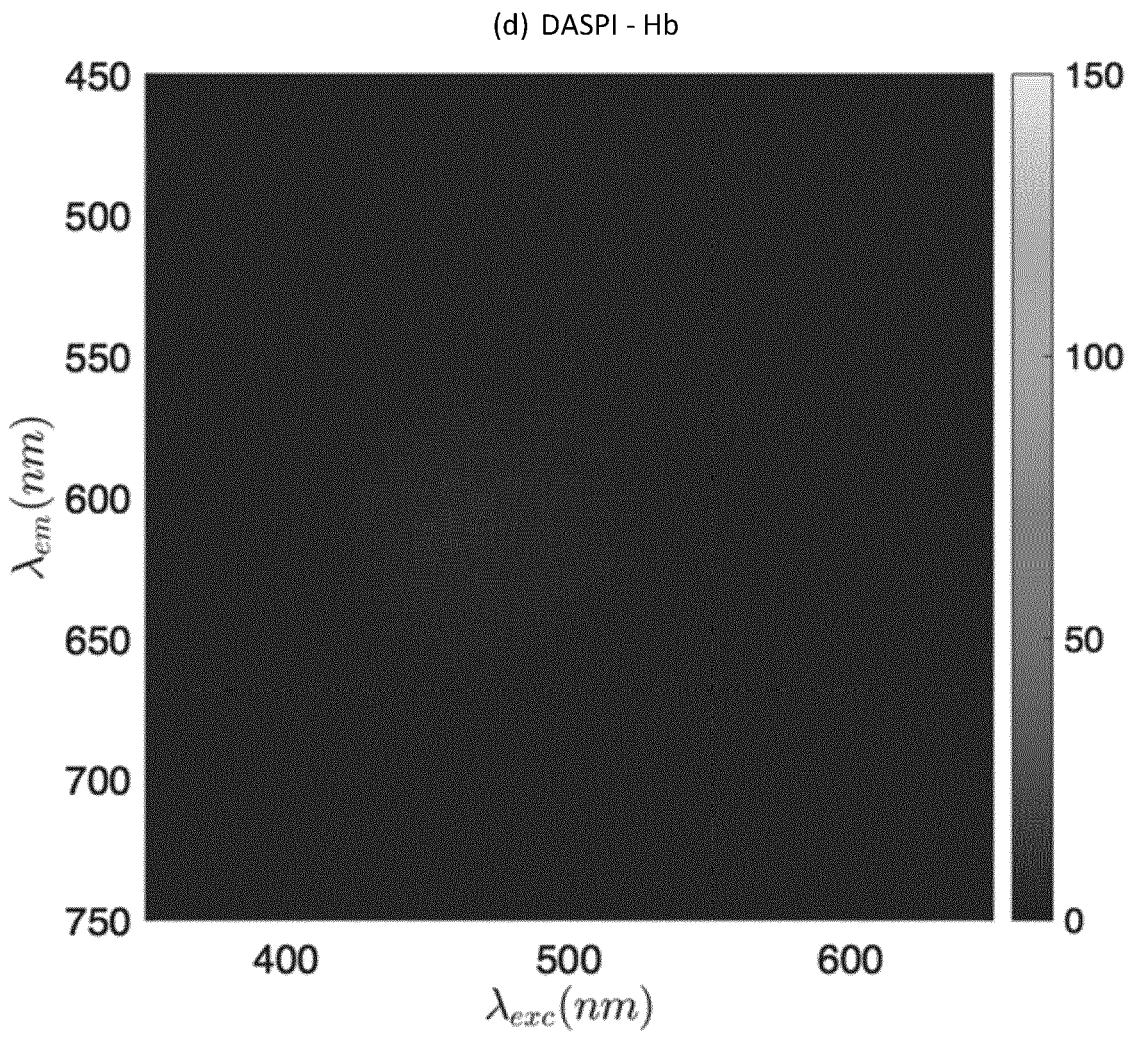
Figure 9E:
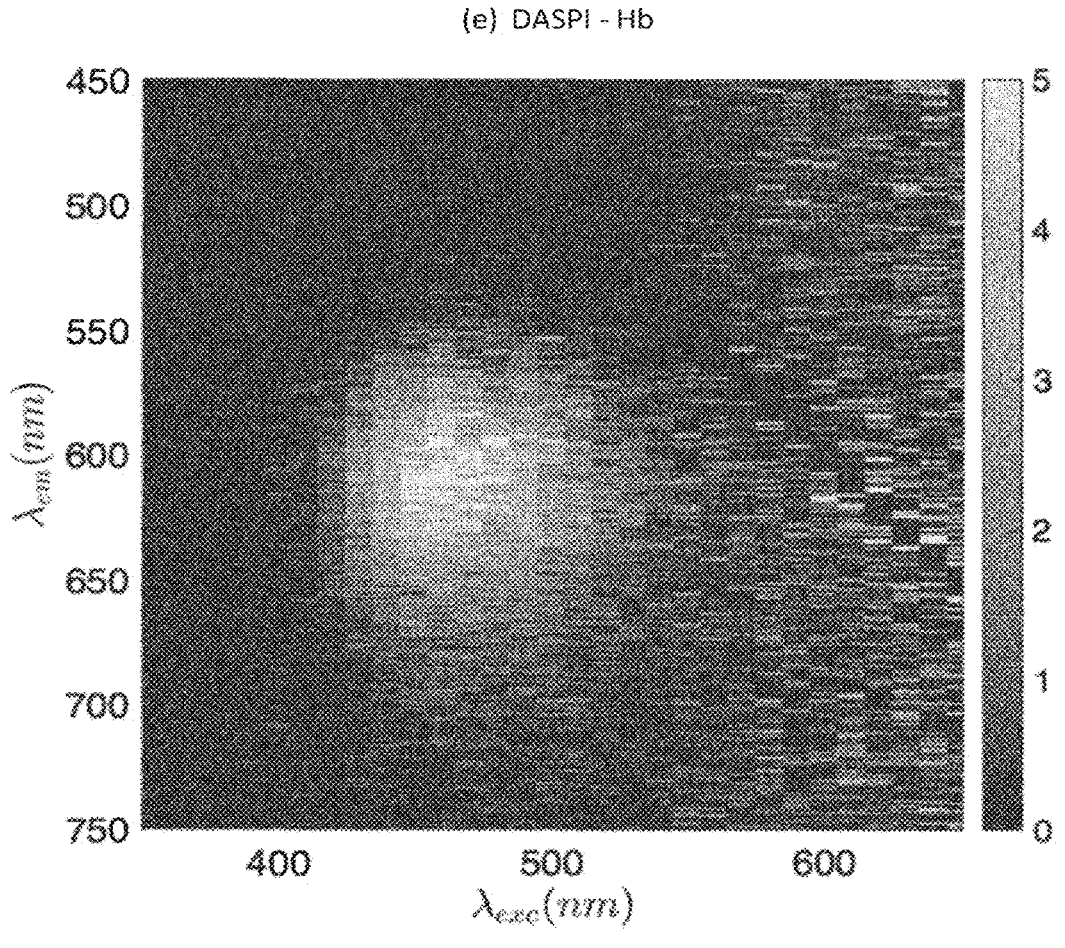
Figure 9F:
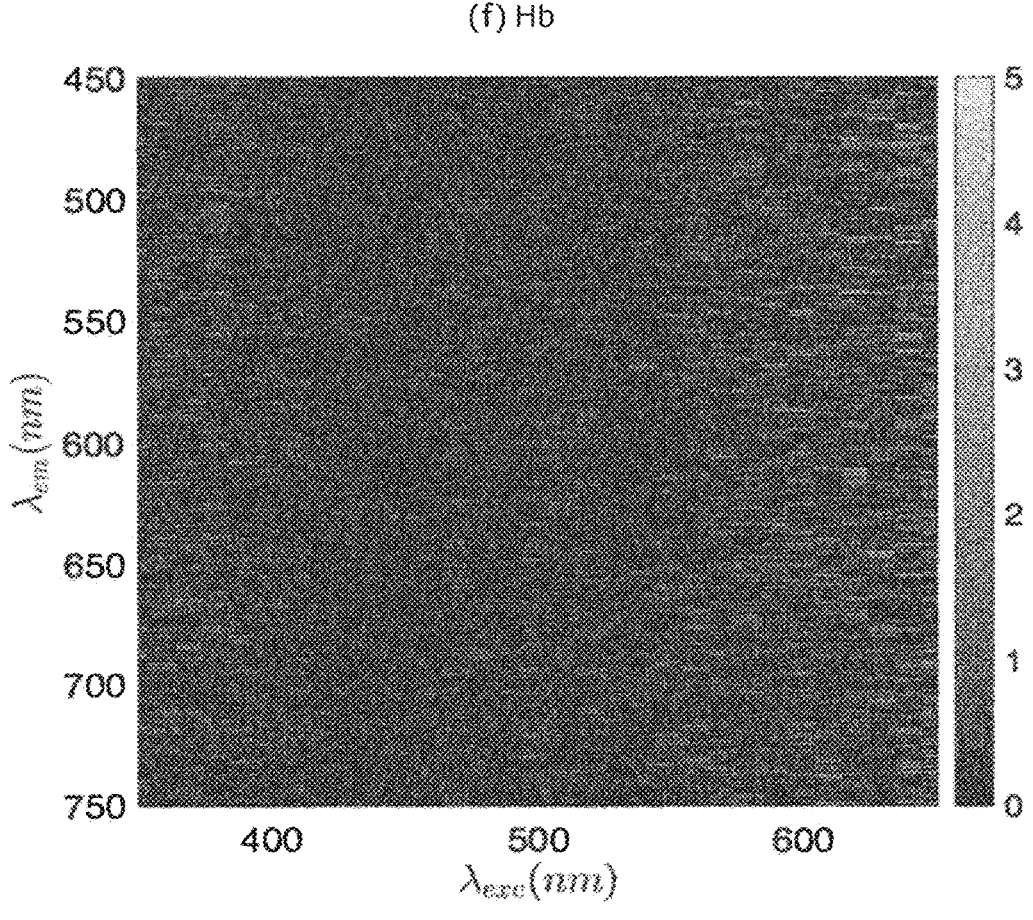

FIG. 8: Normalized mean fluorescence intensity of RBCs with increasing normalized glutaraldehyde concentration. The glutaraldehyde introduced in the RBC suspension result in increasing RBC stiffness revealed by the increasing fluorescence intensity.

FIGS. 9a-9f: Excitation emission matrices of the molecular rotor DASPI, at temperature 25° C., at concentration 3.3 μM in (a) DMSO (η=2 mPa·s), (b) Ethylene glycol (η=13.5 mPa·s), (c) Glycerol (η=945 mPa·s) and (d,e) Hemoglobin in PBS (1000× dilution, different scale, η=1 mPa·s). The Fluorescence EEM of hemoglobin alone (f) was also measured to give evidence that there is no contribution of hemoglobin in the DASPI range of interest. As can be seen, the fluorescence emission intensity (a,b,c) generally increases with the solution viscosity, measured in situ with microrheology experiments. In hemoglobin solutions however (d,e), the emission peak value is lower than in DMSO for similar viscosities because of the high absorbance of the solution.

Figure 10A:
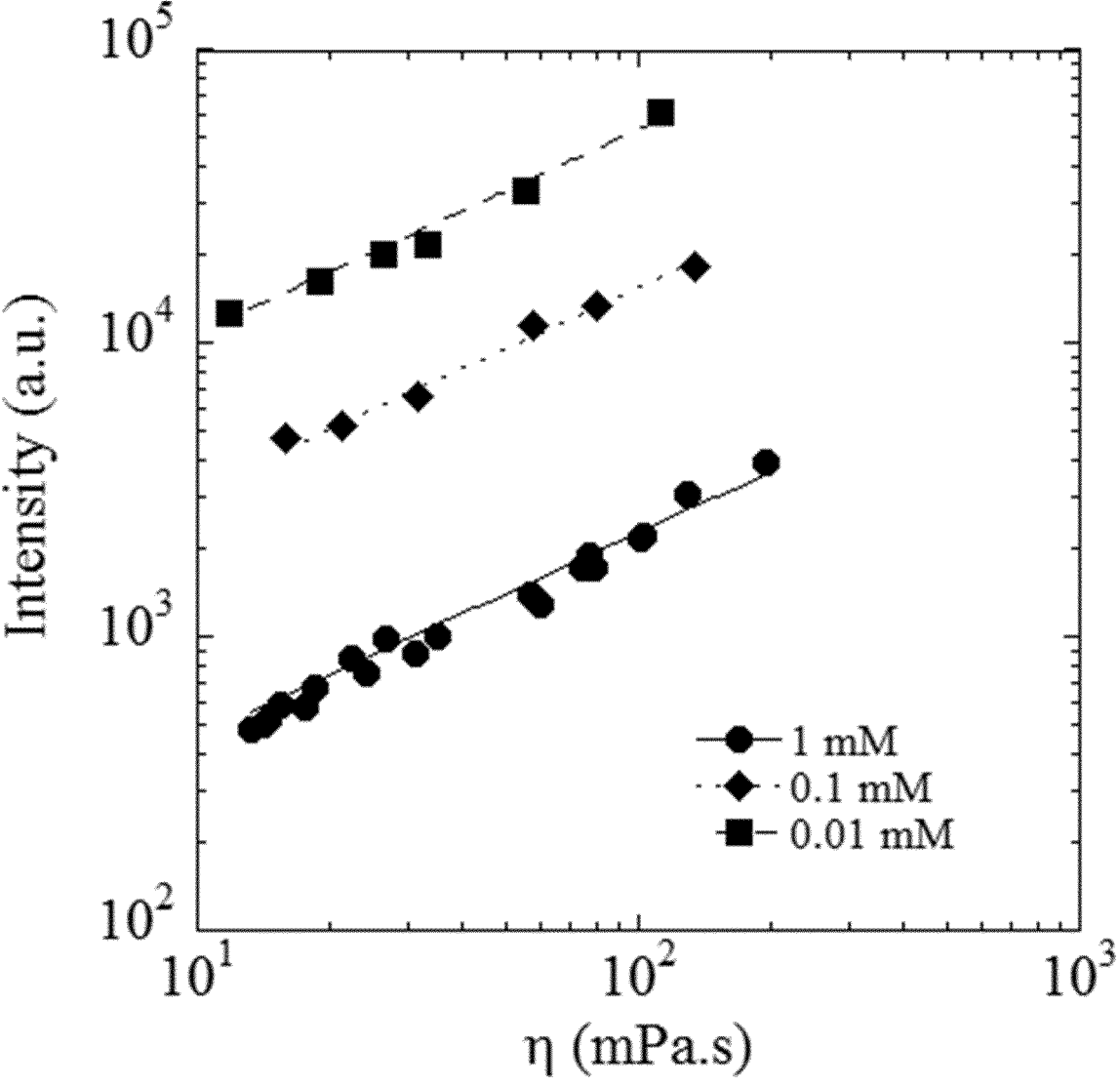
Figure 10B:
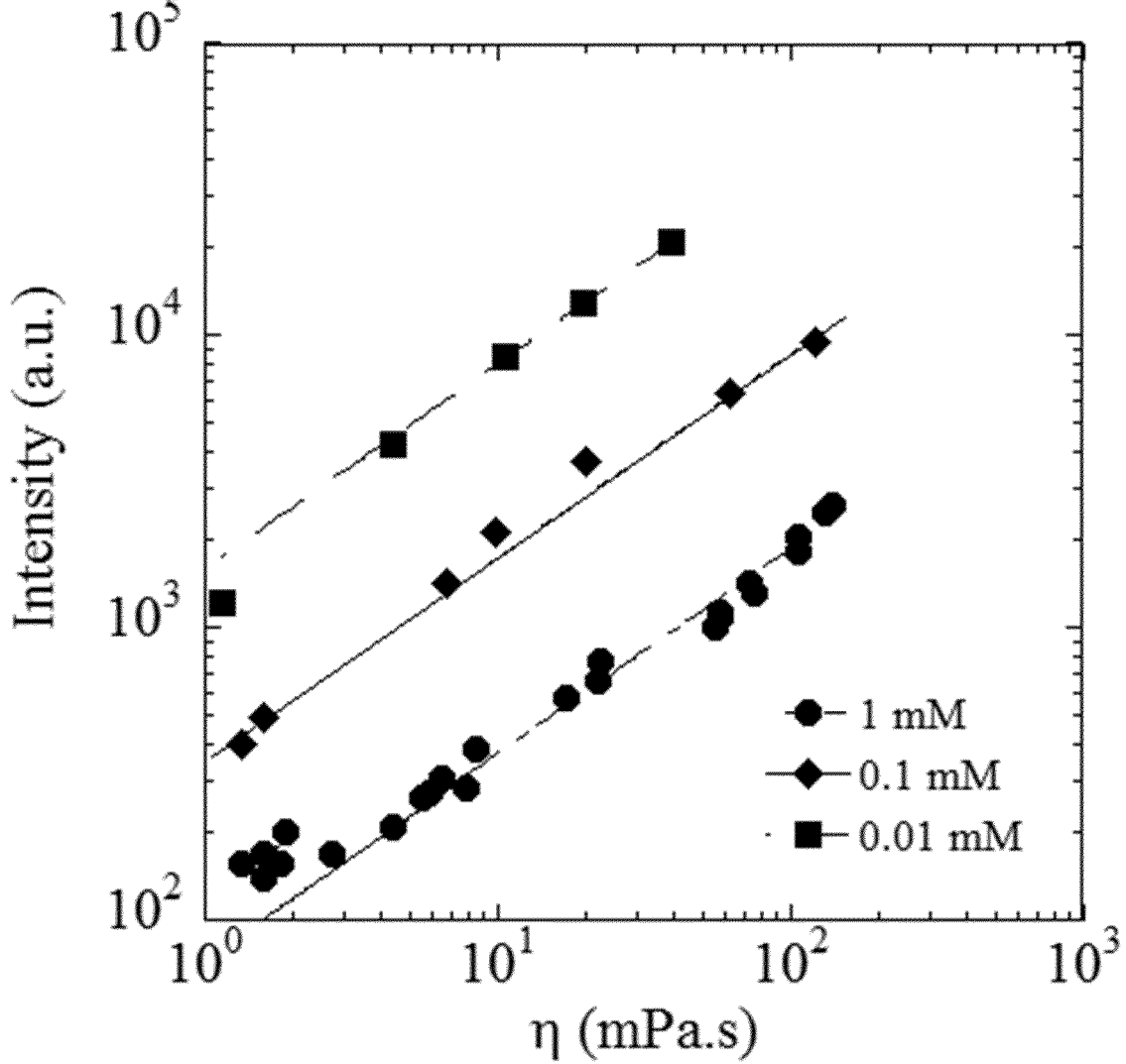
Figure 11A:
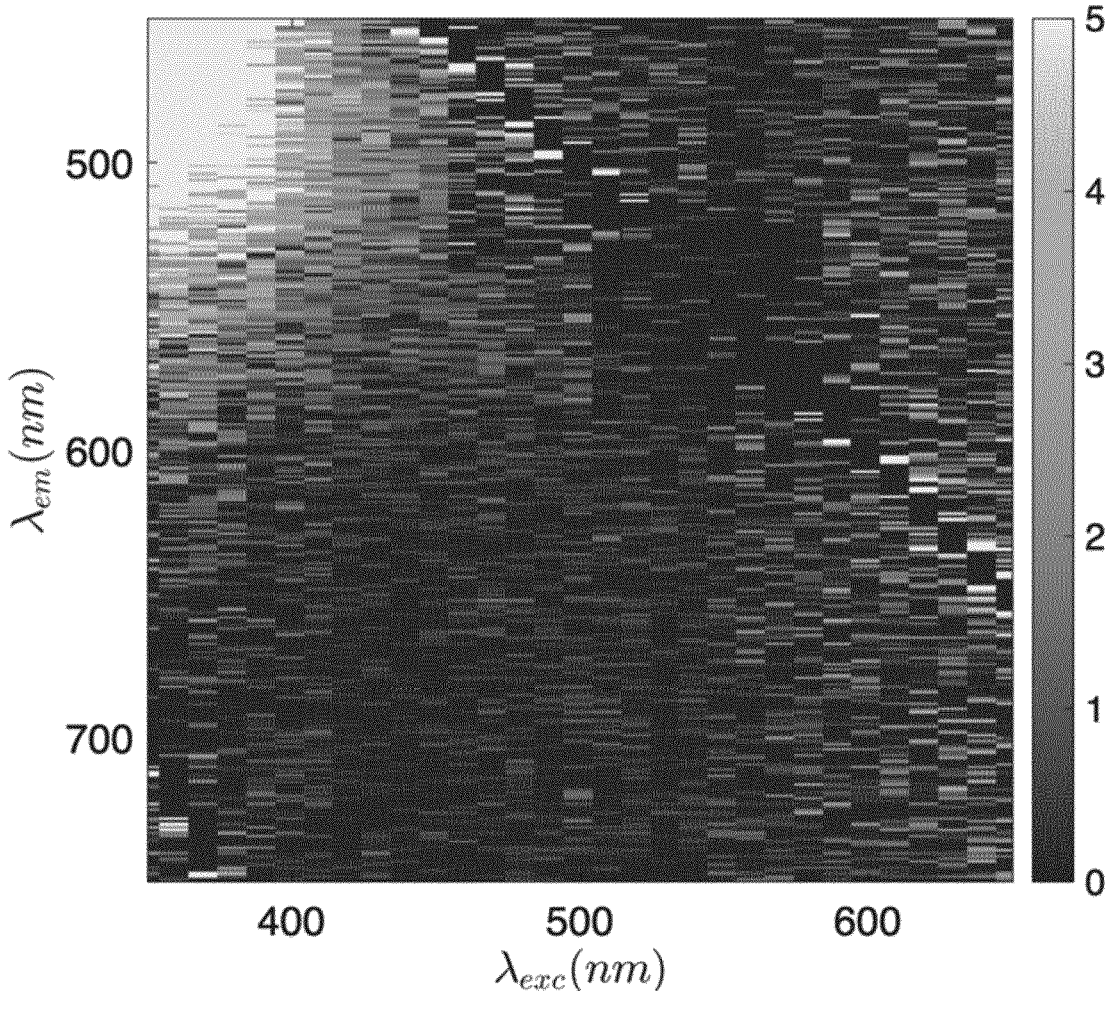
Figure 11B:
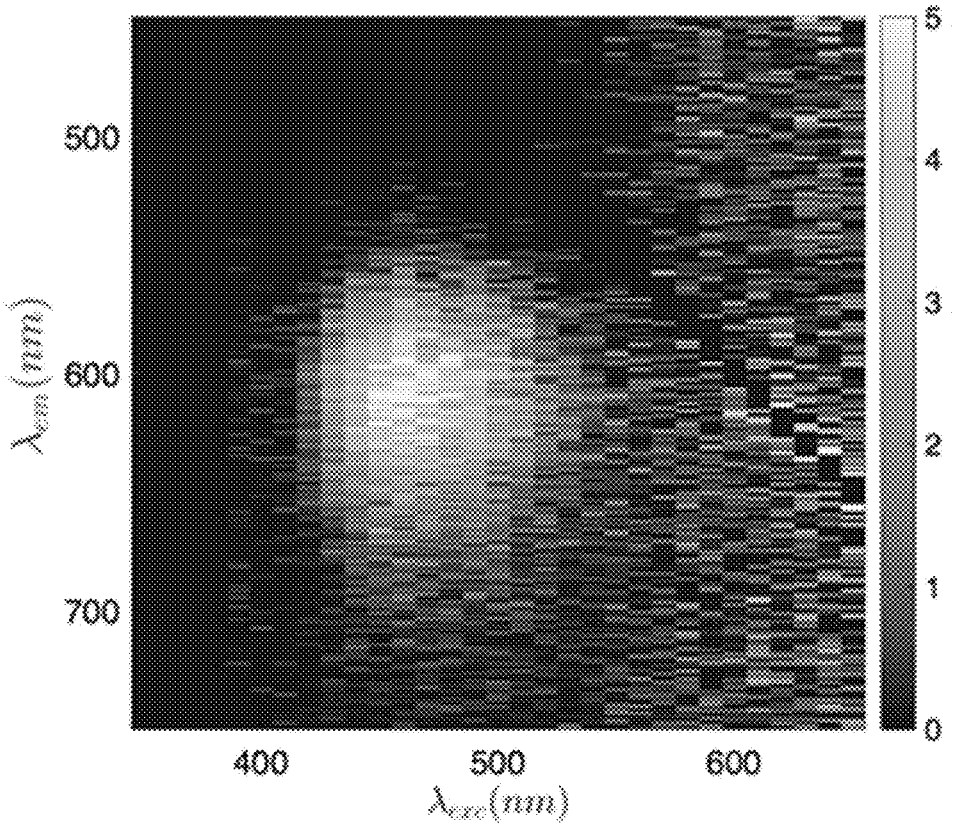
Figure 11C:
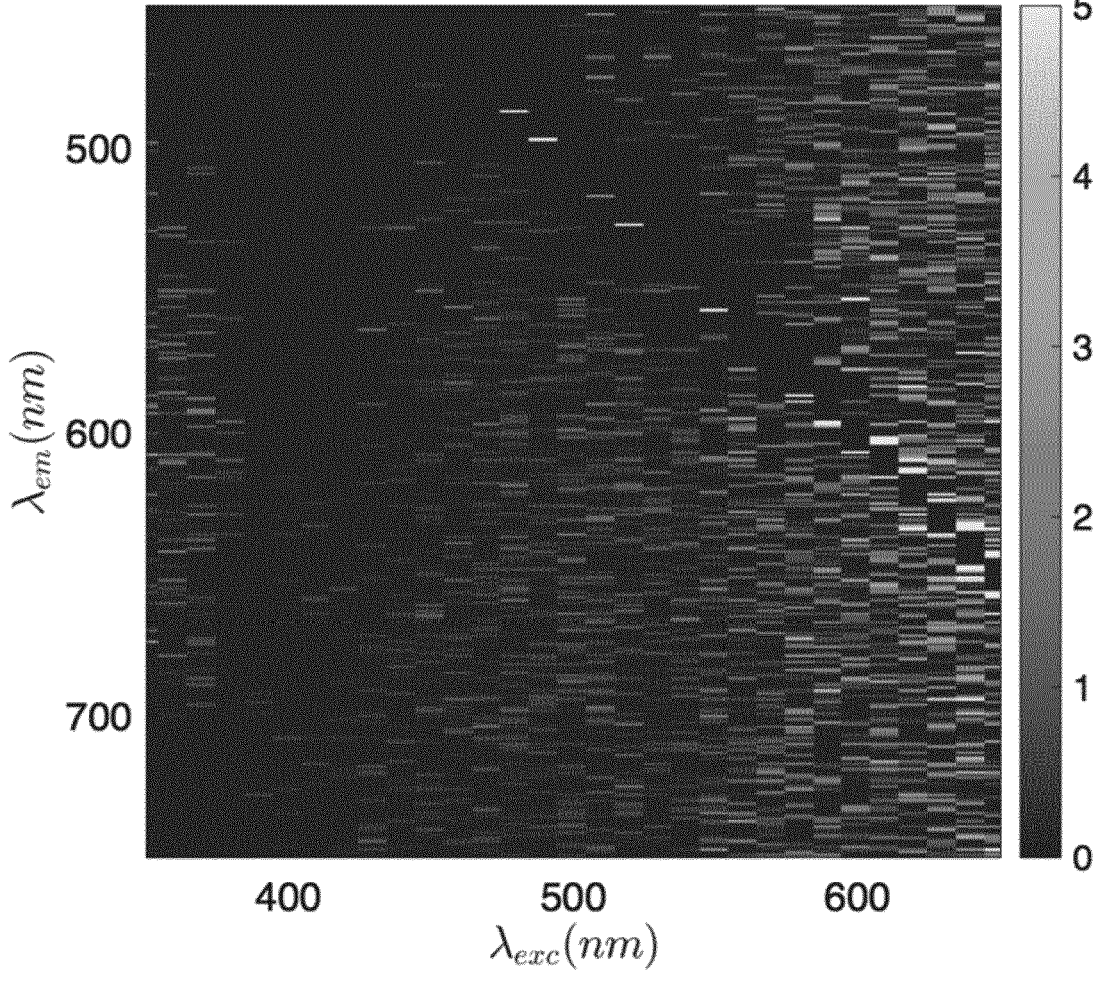
Figure 11D:
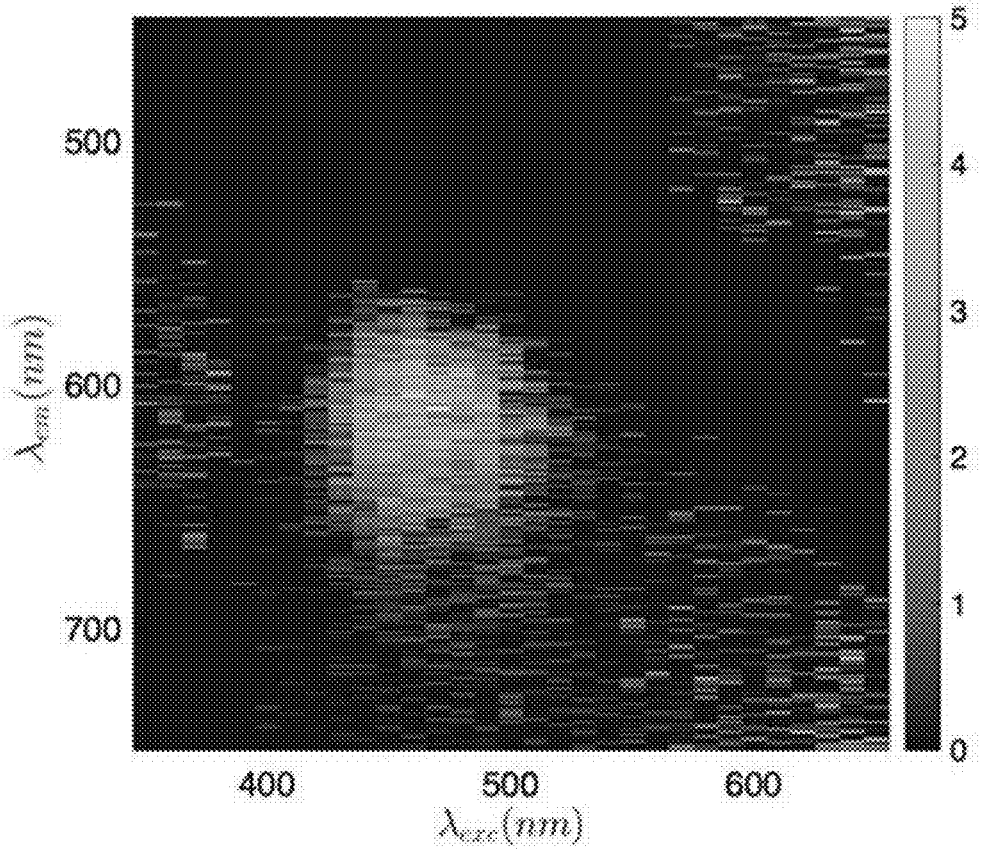
Figure 11E:
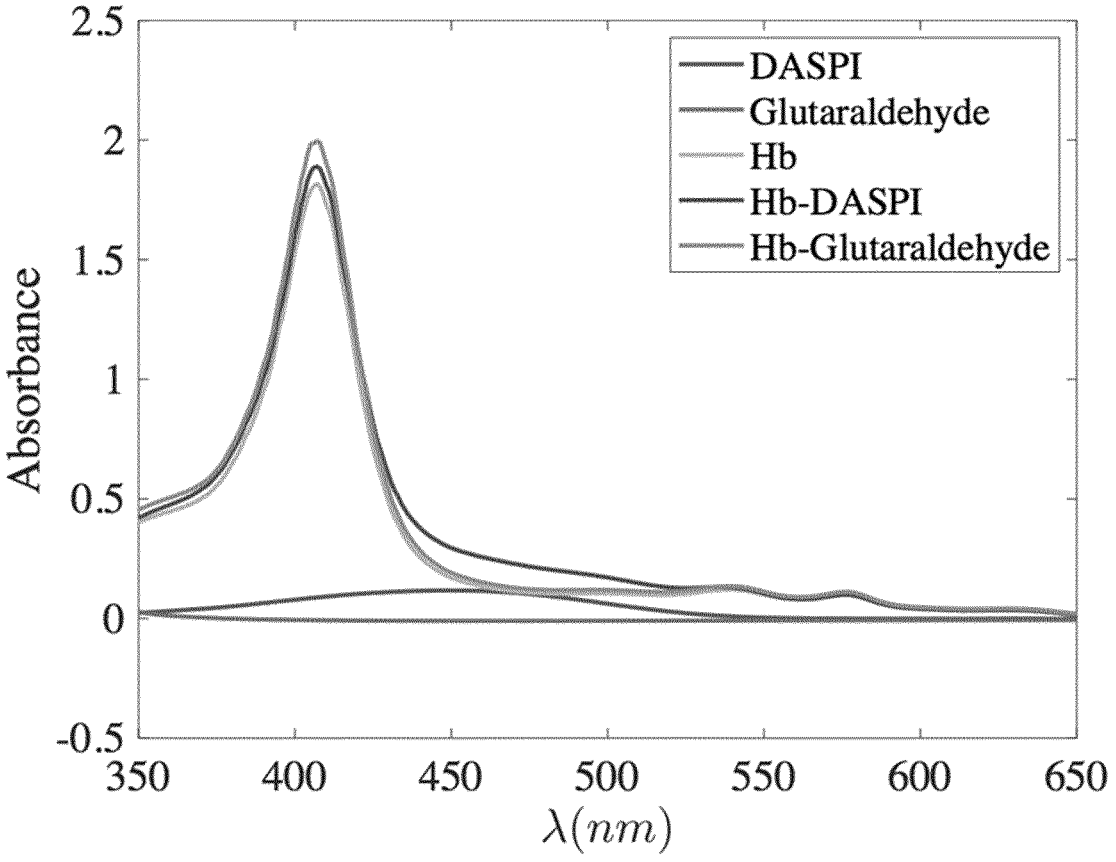

FIGS. 10a-10b: Emission peak intensity (fluorescence microscopy, excitation at 488 nm, emission 595±30 nm) of the molecular rotor DASPI at concentration 0.01 mM, 0.1 mM, 1 mM in (left) ethylene glycol/glycerol solutions and (right) aqueous glycerol solutions with increasing viscosity. The solutions temperature was fixed at T=X ° C. The fluorescence intensity increases with the solution viscosity according to the Förster-Hoffmann equation log φ=C+b log η, with solvent-dependent parameters b and C; Ethylene glycol/glycerol solutions: C=94,641,2206± and b=0.69±0.01 and aqueous glycerol solutions:

$$C=74,344,1590\pm \text{ and } b=0.70\pm0.01.$$

FIG. 11a-11e: EEM spectra in the DASPI range of interest of the following solutions: (a) glutaraldehyde, (b) hemoglobin/glutaraldehyde, (c) hemoglobin/DASPI and (d) hemoglobin/glutaraldehyde/DASPI. The absorbance spectra (e) validates the presence of the various compounds in the solutions and demonstrate that glutaraldehyde does not absorb any signal in the range of interest of DASPI.

Figure 12A:
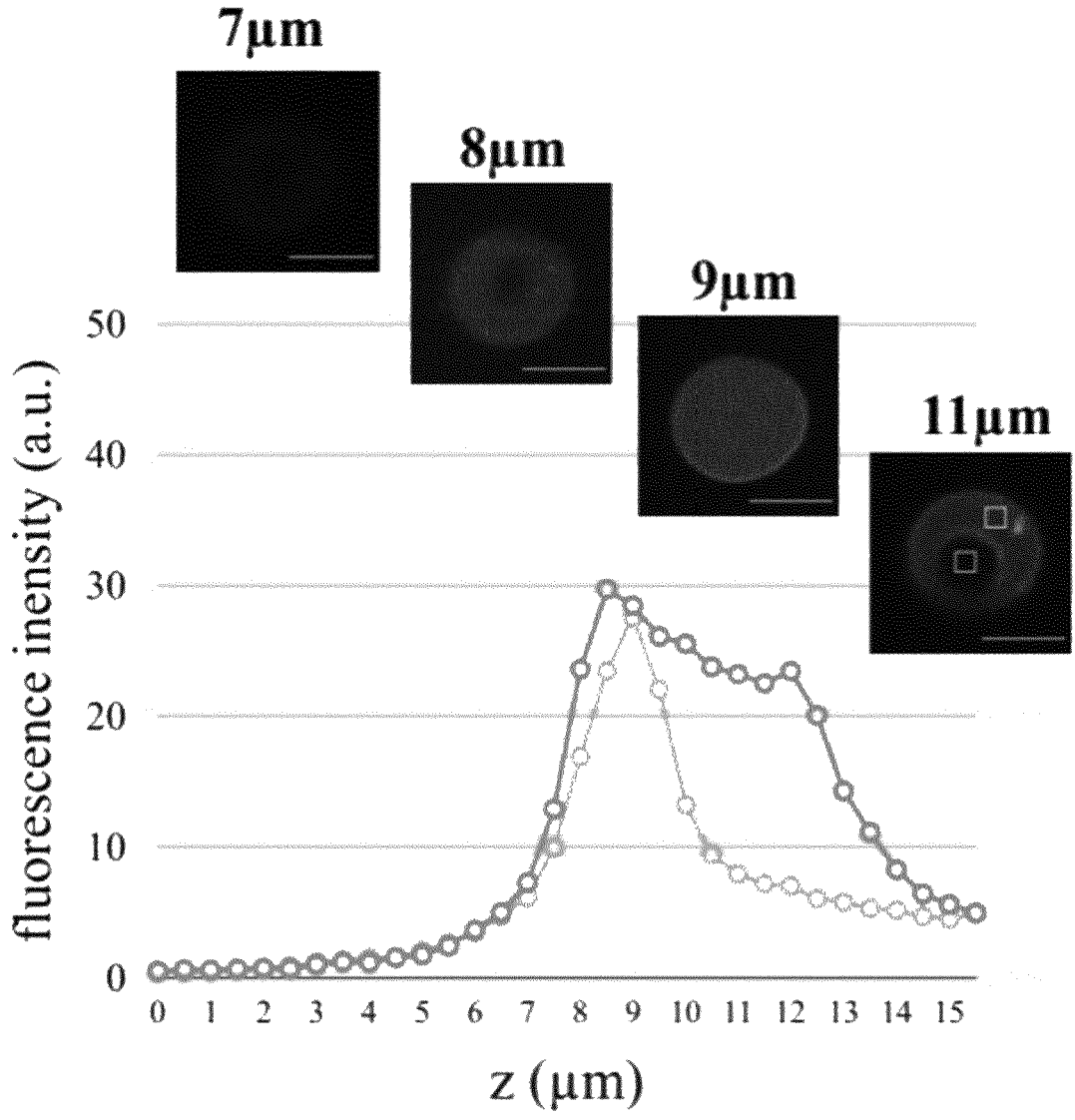
Figure 12B:
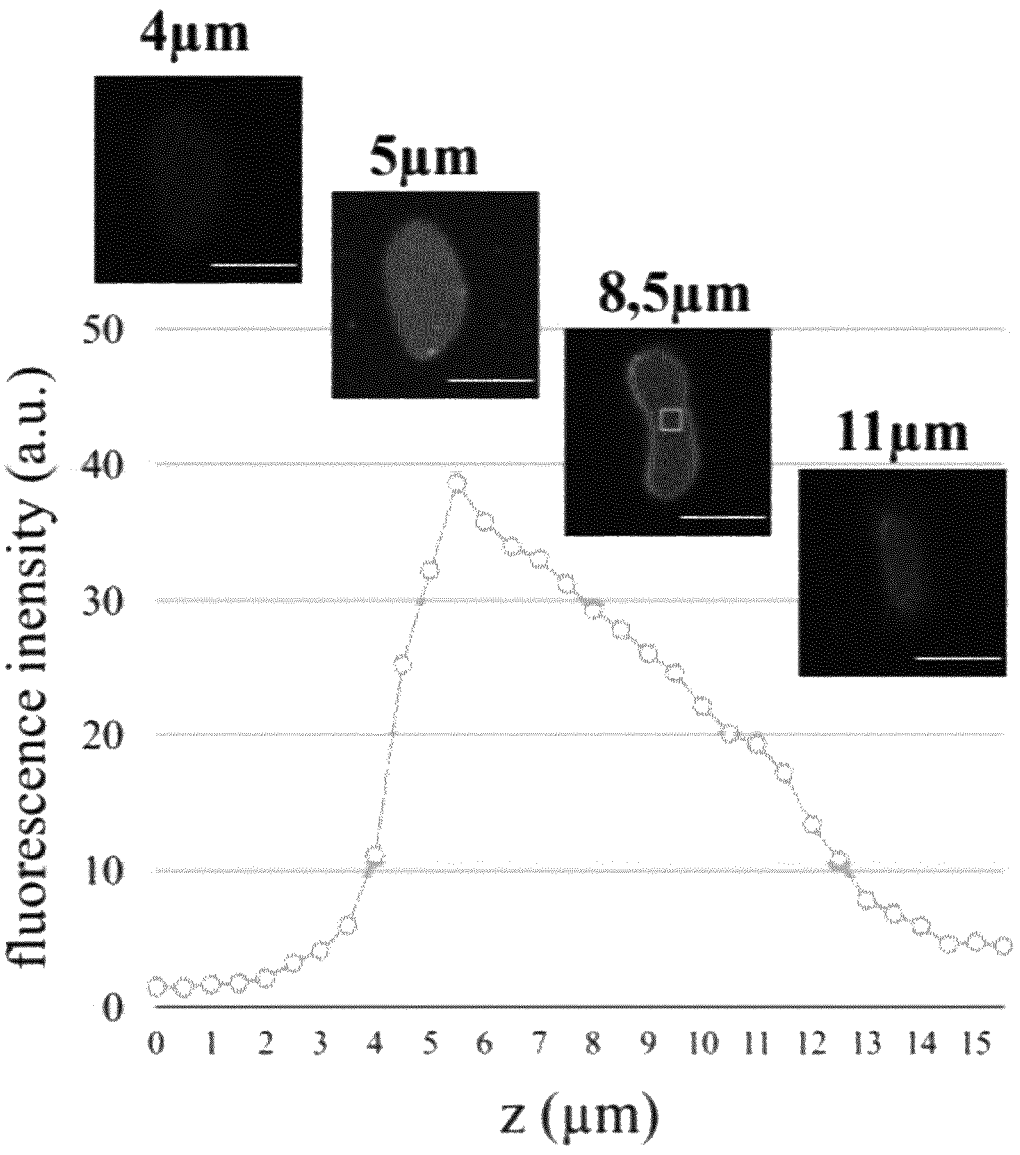
Figure 12C:
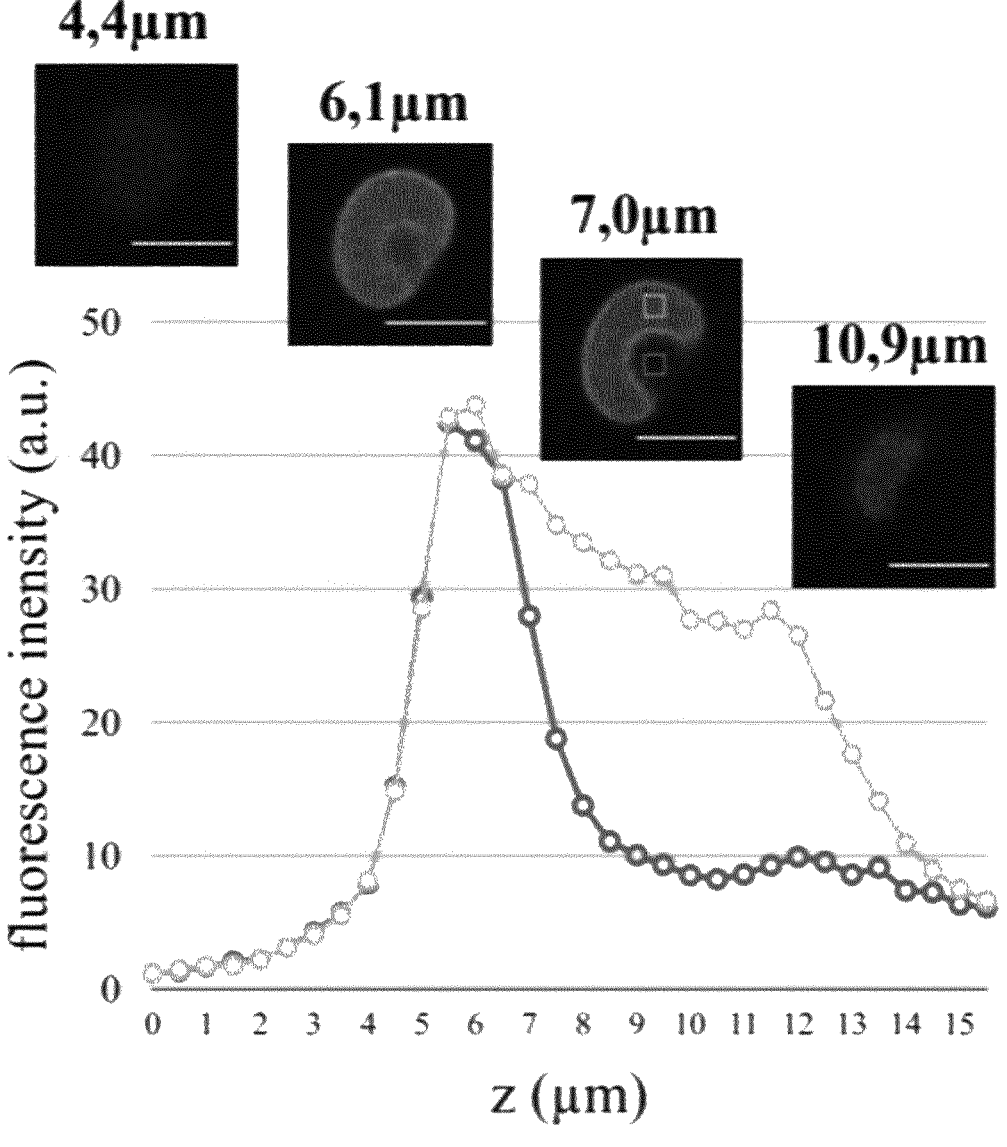

FIG. 12: Bright field image and confocal z-stacks obtained using confocal microscopy (X40 objective, excitation at 488 nm, detection between 542-626 nm) for three healthy RBCs with different orientations in a 1 mM DASPI solution. The z position of the slices is indicated. On the right, fluorescence intensity profiles in the z direction are displayed. The mean intensity was measured in the depicted color boxes and each data point corresponds to a confocal slice (0.5 μm distance).

Figure 13:
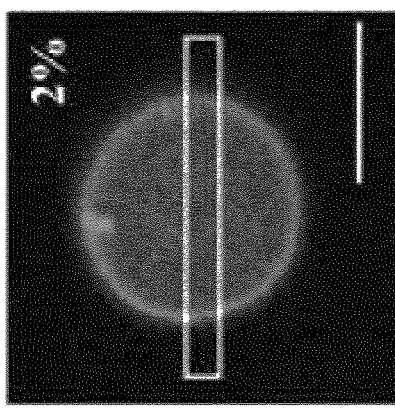
Figure 13:
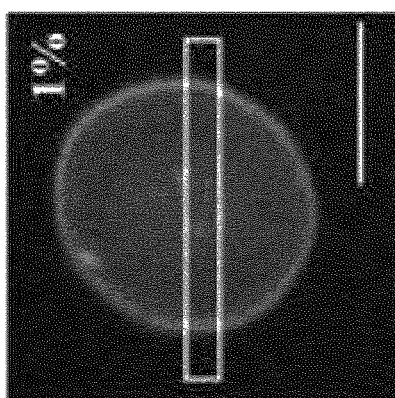
Figure 13:
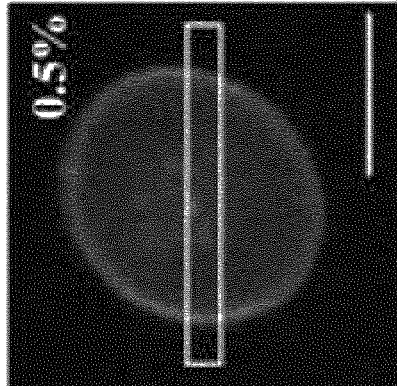
Figure 13:
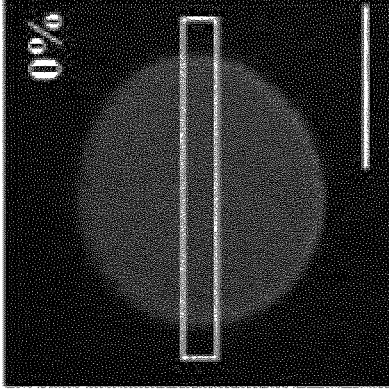

FIG. 13: FIG. 13 shows central confocal sections of stiffened red blood cells with an increasing concentration of glutaraldehyde, as well as their intensity profiles. The concentration of glutaraldehyde was varied between 0 and 2% of the RBC volume, effectively sweeping a significant range of stiffening. We were able to measure that the fluorescence signal inside the cell was uniform in the observation plane at all concentrations of glutaraldehyde indicating uniform penetration of the molecular rotor. The intensity profiles of the central slices all show a homogeneous plateau inside the cell, with sharp peaks corresponding to the membranes.

Figure 14:
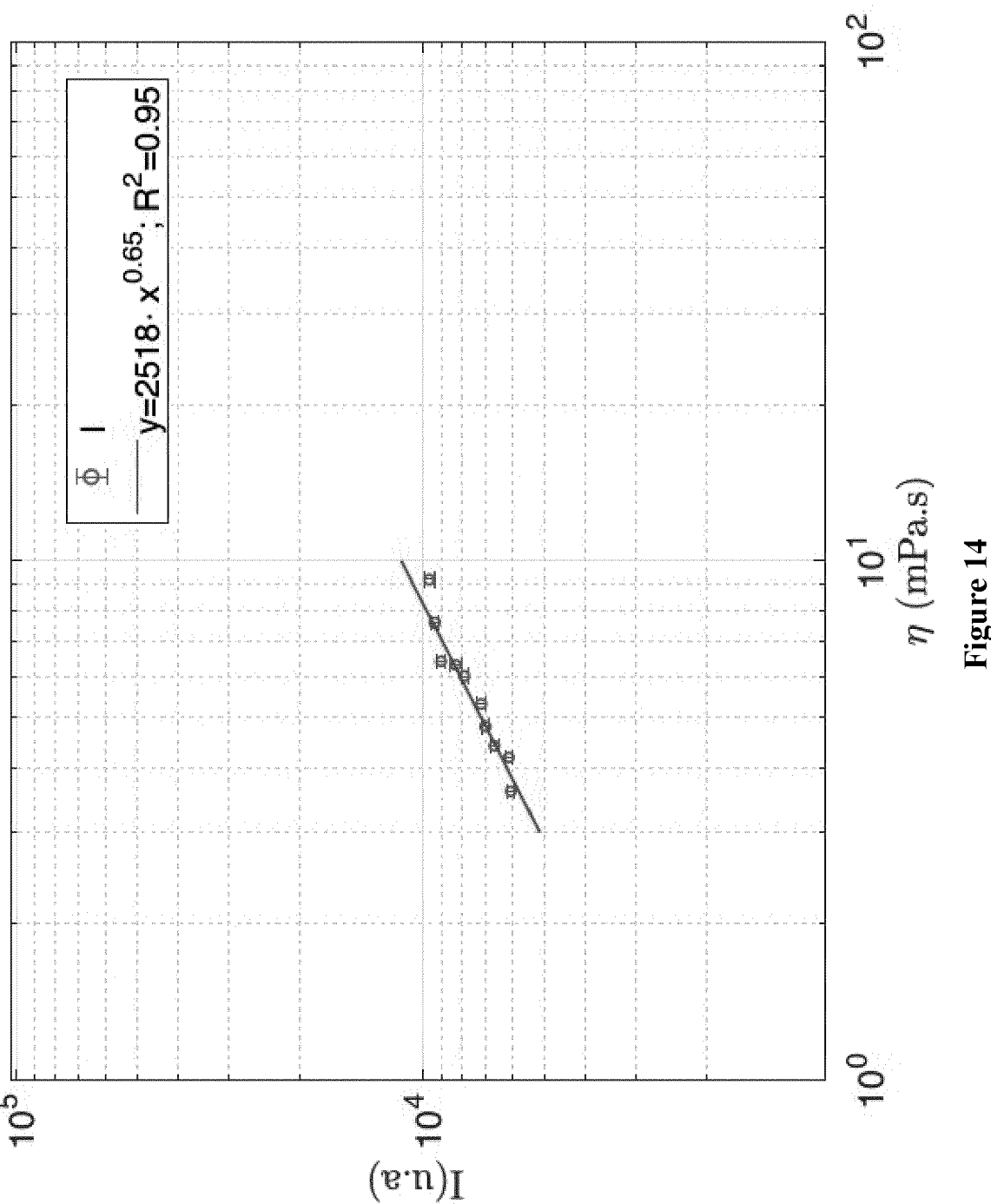

FIG. 14: FIG. 14 shows the increase in fluorescence emission intensity of tDASMP, measured by bright field microscopy, with the increase in viscosity of the hemoglobin solutions.

Example 1: Test of 4 Molecular Rotors (MRs)
Under Variable Biologicals Parameters 1) Determination of the Spectral Response of Commercially Available MRs The determination of the spectral response of the following commercially available MRs has been investigated:

Dicyanovinyl-Julolidine (DCVJ)
Carboxycyanovinyl-Julolidine (CCVJ)
Thioflavine T (Tht)
trans-4-[4-(Dimethylamino)styril]-1-methylpyridinium (tDASMP).

The choice of rotors from the literature was based on the following criteria: low cost, various chemical structures to investigate behaviours and specificity.

The excitation-emission matrix of these 4 rotors, diluted in a glycerol/water solution (purely viscous fluid), have been measured using a SYNERGY H1 (Hybrid Multi-Mode reader, BioTek).

Each rotor exhibits a specific excitation-emission pattern, related to its structure and specificity (see FIGS. 1A-1D), that needs to be considered along with the spectral properties of the medium of application.

The spectral response of 4 commercially available MRs and their sensitivity to parameters relevant in biological environments (viscosity, pH, ionic strength and Albumin concentration mimicking protein-rich environment and its interactions) were investigated. We have identified at least one suitable rotor, not overlapping the haemoglobin fluorescence spectral response. Confocal microscopy experiments showed that MRs penetrate through RBC membranes (FIG. 7). Besides, quantitative fluorescence measurements demonstrate their sensitivity to RBC rigidity (FIG. 8)), demonstrating they are performant biomarkers for a direct measurement of the RBC rigidity.

2) Sensitivity of the Rotors to Parameters Relevant in Biological Environments: Viscosity, pH, Ionic Strength and Albumin Concentration (Mimicking Protein-Rich Environment and its Interactions)

Since the process of twisted intra-molecular charge transfer (TICT) involves the appearance of charges on the molecule, the presence of ions in solution may stabilize the twisted form and decrease the fluorescence signal regardless of the viscosity. Another scenario is that molecular rotors are small hydrophobic molecules that can preferentially be localized in membranes or adsorb to proteins. In such cases, the rotors would exhibit a high fluorescence signal regardless of the rheological parameters of the surrounding medium. Nevertheless, once these biological and physicochemical perturbative effects are calibrated, relative measurements of viscosity variations can be measured.

The fluorescent response spectra of the rotors has been measured by varying four parameters Viscosity, with water-glycerol solutions with increasing relative concentration (see FIGS. 2A-2D);

Electrostatic and ionic perturbations, with increasing NaCl concentration in a water-glycerol solution (50%-50%) (see FIG. 3A));

pH, with buffered solutions Citric acid/Phosphate pH; 3<pH<8 in a water-glycerol solution (70%-30%) (see FIG. 3B); and Molecular density and highly interacting (including hydrophobic) environment using a gradient BSA (bovine serum albumin) (see FIG. 4A-4D).

In these tests, the parameters range was chosen following criteria of biological significance.

Temperature was set to T=37° C. Molecular density was mimicked with Albumin (up to 60 mg/mL, a biologically relevant range), a most represented protein in biological fluids and also the most likely to interact with the rotors because of its physiological role.

In order to get insight on ionic and electrostatic effects on the rotor response (which may vary significantly in biological media), NaCl concentration was increased up to 200 mM. The pH was assayed from 3 (corresponding to the most acidic zones) to 8. For viscosity, we used literature data agreeing on apparent values in various cellular media, ranging from 1.5 mPa·s in the cytoplasm up to 140 mPa·s in the vesicles. In our studies, the MR concentration was set to 15 µM under the expected toxicity onset [Haidekker (2010a)]. One key remark, as any fluorescent molecule, signal intensity is also a function of its concentration. It is therefore very important to control the concentration of molecular rotor or, if when impossible, to be able to measure the concentration regardless of the viscosity.

All the investigated rotors were found to be very sensitive to viscosity, following the Förster-Hoffmann equation (see FIG. 2A-2D). This confirms that they are possible probes for the quantitative viscosity determination according to the present invention.

In the range investigated for pH (3-8) and ionic strength (0.1-200 mM), the MRs showed no significant sensitivity to these two parameters (see FIG. 3A-3B).

After checking that the solution viscosity does not vary with BSA concentration in the studied range, it has been found that most of the rotors were sensitive to BSA (FIG. 4A-4D). The fluorescence intensity depends on BSA concentration, at least in part of the concentration range, with no relation to viscosity. This indicates that MRs can specifically interact with proteins.

Example 2: Test of Molecular Rotors on Red Blood Cells

Haemoglobin, the major component of red blood cell cytoplasm is known to exhibit relatively rich absorption and fluorescence spectra that may interfere with MR characteristics. We performed measurements of the EEM of suspensions of washed healthy RBCs, pathological RBCs obtained from a HbSS homozygous patient, and the corresponding full blood samples (FIGS. 5A-5D) to determine their emission-absorption spectra. To do so, the two blood samples were diluted in PBS (Phosphate Buffered Saline from Sigma-Aldrich) and centrifuged at 1000 g and this procedure was repeated three times to produce the washed-RBC samples. Molecular rotors were dissolved at 40 mM in DMSO (dimethyl sulfoxide) and added to samples in order to reach a concentration of 0.2 mM. EEM (Excitation-Emission Matrixes) were then obtained using a Biotek Synergy H1 Hybrid Multi-Mode Plate Reader.

Among the different rotors investigated, tDASMP was identified as the preferred candidate to investigate RBC deformability, with an excitation peak around 490 nm, and emission between 580-620 nm which are significantly separated from the emission-absorption spectra of full blood and RBCs that are visible in FIGS. 5A-5D.

As a next step towards the rheological characterization of RBCs with MRs, we then imaged a suspension of healthy and artificially rigidified RBCs (by incubation during 10 min in a 1% (v/v) Glutaraldehyde solution in PBS) treated with tDASMP. Healthy and rigidified RBC suspensions were mixed and the resulting suspension was observed using confocal microscopy with an excitation at 488 nm and detection between 546 nm and 626 nm. An image corresponding to the mid-cross section of the RBC after cells have sedimented on the bottom window of the observation chamber is shown in FIG. 6. It shows a strong difference of fluorescence level of cells between rigid (brighter) and healthy (darker) cells. Confocal microscopy allows to measure fluorescence profiles across RBCs. Typical profiles for normal (healthy) and hardened RBCs are shown in FIG. 7.

The fluorescence intensity was found to be 10 times higher for stiffened RBCs than for healthy ones (see FIG. 7), giving evidence that the rotor is sensitive to the rigidity of the RBCs.

In addition, these confocal measurements give evidence that, as expected, the molecular rotor was able to cross the membrane and penetrate within the RBCs, with a slightly higher level of fluorescence on the membrane (sharp edges on the fluorescence profiles) that possibly reveals interactions of the MR with the spectrin network or components of the membrane. Remarkably, for rigidified cells, the fluorescence profile is dominated by the cytoplasm. It is demonstrated by the absence of the edge peaks (membranes) and a signal that varies with the local thickness of the cell.

In a second step, a quantification of the fluorescence response as a function of the degree of rigidification of RBCs can be performed. RBCs were washed three times by dilution in phosphate buffer saline (PBS) and centrifugation at 1000 g and finally re-suspended in PBS to reach a hematocrit value of 5%. A working solution of 1% glutaraldehyde in PBS was prepared by diluting a stock solution at 50% glutaraldehyde concentration (G7651 from Sigma-Aldrich) in PBS. Washed RBCs were treated with glutaraldehyde by adding an appropriate volume of glutaraldehyde working solution to 5% hematocrit suspensions of RBCs in order to reach final concentrations between 0 and 2% of glutaraldehyde per volume of cells. The suspensions were then incubated for 10 min at room temperature, washed twice in PBS to remove unreacted glutaraldehyde and resuspended in PBS at a hematocrit of 0.2%. A stock solution of 40 mM tDASMP or DASPI (trans-4-[4-(Dimethylamino) styryl]-1-methylpyridinium iodide, ref 336408 from Sigma-Aldrich) in DMSO was prepared and then diluted in PBS to make a 8 mM working solution. The aforementioned glutaraldehyde-treated RBC suspensions were stained by adding 5% (v/v) of 8 mM DASPI solution, yielding a final concentration of 0.4 mM DASPI in samples, and incubated for 1 hour at room temperature to let DASPI diffuse through RBC membranes.

For visualization, samples were placed between a glass slide and coverslip separated by a 250 µm spacer and initially incubated in a PBS solution supplemented with 1% BSA (Bovine Serum Albumin, Sigma-Aldrich) to prevent RBC adhesion. Observation was made with a Leica microscope in epi-fluorescence mode with excitation at 488 nm and detection at 565-625 nm. Images recorded with a sCMOS fast camera (OrcaFlash4.0 v2+, Hamamatsu Photonics France S.A.R.L., Massy, France) allowed to measure the mean fluorescence intensity of RBCs rescaled by the background fluorescence level. The normalized mean intensity for increasing concentrations of glutaraldehyde (corresponding to increasing cross-linking of proteins in the RBCs and therefore increased rigidity) is represented in FIG. 8 and shows that the fluorescence intensity is an increasing function of RBC rigidity.

All together, these experiments constitute a proof of concept that MRs can be used as nanoscale rheological probes in biological environments and especially RBCs. They are able to penetrate cell membranes and to provide a fluorescent signal sensitive to local compartment rheology and their use in a context of cellular viscosity assessment is a promising perspective.

Example 3: Blood Sample Characterisation by MRs and Clinical Profiles

1) The Systematic Comparison of Blood Sample Characterisation by MRs and Clinical Profiles can be Easily Performed For example by analysing the fluorescence intensity obtained for RBCs cytoplasm from healthy patient blood sample, compared with (stiffened) RBCs cytoplasm from blood sample of:

(i) patients in the basal state without background treatment and out-of-crisis, and by comparing different phenotypes of sickle cell disease (SS, SC, Sβ°, Sβ+ . . . )

(ii) patients in vaso-occlusive syndromes, from which two large clinical severity cases can be distinguished (vaso-occlusive crisis, acute thoracic syndrome)

(iii) In non-crisis patients undergoing treatment (i.e. iatrogenic iron deficiency anemia);

(iv) women outside and during pregnancy, and in combination with appropriate statistical analyses.

This will qualify the tests in terms of sensitivity and specificity and will allow to situate this new test among the current diagnostic or prognostic tools.

Example 4: Quantification of the Correlation Between the Fluorescence Response of Molecular Rotors and Rheological Properties 1) Robust Calibration of MRs Based Viscosity Measurements using Micro-Rheology Technology To this end, controlled viscosity solutions will be prepared using a set of glycerol concentrations. As well we will enlarge robustness studies by measuring rotor response perturbations with biological solutions (or extracts) close to red blood cell intracellular medium. In particular, the effect of interactions will be investigated with blood proteins, especially haemoglobin, on the rotor properties.

Selection of a new molecular rotor or chemical modification of existing molecular rotor.

2) Optimize the Labelling of Red Blood Cells by Molecular Rotors

Molecular rotor performances will be evaluated. In particular, the rotor sensitivity to viscosity changes can be investigated under complex environments, as well its capacity to cross the red blood cell membrane, to remain in solution into the cell. In addition, the intracellular amount of rotor can be evaluated to analyze the fluorescence signal.

Example 5: DASPI Molecular Rotor Properties, Particularly in Red Blood Cells 1) DASPI Molecular Rotor Properties
1.1 Spectral Properties The molecular rotor DASPI (trans-4-[4-(dimethylamino)-styryl]-1-methylpyridinium iodide, 336408 from Aldrich) from the stilbenes group, was selected for its fluorescence spectral properties compatible with those of hemoglobin, which is known to have a broad absorption spectrum and intrinsic fluorescent properties in the ultraviolet range.

In a first step, fluorescence Excitation Emisson Matrices (EMMs) of DASPI were measured in selected solvents, at controlled temperature 25·C: DMSO, Ethylene Glycol, Glycerol and hemoglobin/PBS solutions (dilution 1000×). FIGS. 9-(a,b,c,e) show that the fluorescence EEM spectra of DASPI are similar from one solvent to another. As displayed in the spectra (a,b,c,e), DASPI is a single band emission molecular rotor, which exhibits fluorescence excitation and emission peaks respectively around 480 nm and 600 nm. Crucially, the excitation-emission spectrum of DASPI in hemoglobin (FIGS. 9-d,e) does not interfere with the intrinsic hemoglobin fluorescent spectrum (known to be in the ultraviolet for which excitation maxima are below 400 nm and emission below 460 nm). The Fluorescence EEM of hemoglobin alone (dilution 1000× in PBS) was also measured in the DASPI range of interest to give evidence that there is no contribution of hemoglobin in this range (f).

From the EEM spectra ($a,b,c$), we can measure that the rotor has a fluorescence emission intensity which increases with viscosity. In hemoglobin solutions however, the emission peak value is lower than in DMSO for similar viscosity (FIG. 1-($a,d,e$)) due to the high absorbance of hemoglobin. The latter remains non-negligible even if the DASPI emissions are optimally located around a minimum of local absorption of hemoglobin (~600 nm, see FIGS. 11$a$-$e$)).

1.2 Förster-Hoffmann Relations for Viscosity

The second step was to assess the sensitivity of DASPI to the local viscosity of the surrounding medium. More generally, fluorescent MRs photophysical sensitivity depends on their interaction with the environment, characterized by viscosity, polarity and solubility. In previous studies however, molecular rotors with a single emission band showed highly viscosity-dependent emission intensity combined with low sensitivity towards solvent polarity. Here we have investigated the DASPI emission intensity (fluorescence microscopy, excitation at 488 nm, emission at 595±30 nm) in ethylene glycol/glycerol solutions (viscosity between 10-200 mPa·s) and aqueous solutions of glycerol (viscosity between 2-200 mPa·s). In each solution, the relative concentration of both solvents was varied to adjust the viscosity of the resulting mixture, at temperature T=X° C. The viscosity was measured in situ by microrheology measurements, just before fluorescence intensity measurements. In ethylene glycol/glycerol solutions, the polarity remains approximately constant as the relative concentration increases, because the polarities of the two liquids (glycerol and ethylene glycol) are similar. However, in aqueous solutions of glycerol, the polarity of the solvent varies with the concentration of glycerol (between x-y%), since water and glycerol have different dielectric constant, and thus polarities (dielectric constants from: water: 80.1, glycerol: 42.5, ethylene glycol: 37.7) FIG. 2 shows that the rotor response follows a Förster-Hoffmann equation, $\log\varphi = C + b \log \eta$ in both solutions, with b and C two solvent-dependent parameters (water/glycerol: C=74,344,1590 and b=0.70±0.01; ethylene glycol/glycerol solutions: C=94,642,2206 and b=0.69±0.01). The exponent b was similar in the two solutions and close to 0.7. The parameter C is specific to the solvent and increases significantly with the DASPI concentration. In ethylene glycol/glycerol solutions where polarity effects are minimized, the decoupling between polarity and viscosity gives evidence that the rotor response is sensitive to, and increases with, the local viscosity. In aqueous glycerol solutions, the polarity is variable and decreases with increasing viscosity, according to the dielectric constant values. Still the rotor response follows a Förster-Hoffmann equation suggesting that the polarity has little effect on the single band emission rotor response, as already shown by Haidekker et al. At low viscosity around 1-2 mPa·s in the aqueous glycerol solutions, a deviation is observed from the Förster-Hoffmann law as already observed in previous studies.

2) Glutaraldehyde-Induced Stiffening and Fluorescence

Glutaraldehyde is a commonly used fixative, known to cross-link proteins and biological materials, which we use here to induce controlled stiffening of red blood cells. It is a non-specific fixative that acts on all components of the cell, and increases the effective viscosity of the cytoplasm and lipid membrane.

3) Molecular Rotor in Red Blood Cells 3.1 Penetration in Healthy Red Blood Cells The localization of the DASPI molecular rotor in healthy red blood cells was studied by confocal microscopy. Confocal images were acquired during the slow sedimentation of the RBCs with different orientations in the observation microchannel. FIG. 12 shows stacks of slices for three different RBCs. The fluorescence signal of the membrane was found to be slightly stronger, due to the interaction between the molecular rotor and the components of the membrane, although interpretation in terms of mechanical properties is difficult at this stage, and beyond the scope of this study. Beyond the membrane, in the cytosol, the signal from DASPI was homogeneous in the observation plane, regardless of the z-position and orientation of the cell. Confocal microscopy allows us to unambiguously separate the fluorescence response from the membrane and cytosol. In fact, as soon as the upper and lower membranes are out of the depth of field (~600 nm), they no longer contribute to the field of vision. This indicates that the fluorescence signal observed inside the cell, far enough from the membrane, comes only from the cytosol, without any signal from the membrane. The molecular rotor is thus uniformly distributed throughout the volume of the red blood cells. Additional evidence of uniform and effective penetration of molecular rotors into RBCs, is provided by the intensity profiles of these red blood cells in the z-direction. By scanning the different parts of the red blood cells, we measure that the DASPI fluorescence signal is present throughout the whole red blood cell, over a distance which corresponds approximately (given the depth of field) to the typical known sizes of the red blood cell: diameter 8 μm (b), thickness on the edge 3 μm (a), thickness in the biconcave zone ~1 μm (a).

3.2 Sensitivity to Stiffening of Hemoglobin and Red Blood Cells

Red Blood Cells were treated with glutaraldehyde to induce controlled stiffening. Unlike most authors who control the concentration of glutaraldehyde in the total volume of fluid60, we have chosen to work with a concentration of glutaraldehyde, defined as a function of the volume of red blood cells. Since glutaraldehyde is a crosslinking agent, reproducibility and intermediate levels of hemoglobin polymerization can only be achieved by fine-tuning the ratio of glutaraldehyde and hemoglobin concentrations to avoid dependence on hematocrit.

3.3 Uniformity of the fluorescence signal inside the cell

We were able to measure that the fluorescence signal inside the cell was uniform in the observation plane at all concentrations of glutaraldehyde indicating uniform penetration of the molecular rotor. The intensity profiles of the central slices all show a homogeneous plateau inside the cell, with sharp peaks corresponding to the membranes (see FIG. 13).

Example 6: Test of the Molecular Rotor tDASMP in Hemoglobin Solutions of Increasing Viscosity Red blood cells were washed three times in PBS buffer in order to prepare hemoglobin solutions from blood samples. After a final centrifugation at 1200 g for 10 min, all the supernatant was removed. The RBC pellet was exposed to 3 freeze-thaw cycles (−80° C. to 37° C.) to lyse RBC membranes. Membrane residues were then extracted by addition of CCl4 to the lysate (⅓ of the volume), strong agitation and ultra-centrifugation at 10000 g for 15 min. The hemoglobin concentration in the final solution was measured by colorimetry (MAK 115 Hemoglobin Assay Kit from Sigma-Aldrich).

We studied the emission intensity of tDASMP in hemoglobin solutions of increasing viscosity. The temperature of the sample was varied between 17° C. and 34° C. This resulted in a decrease in the viscosity of the solutions, from 9.2 mPa·s to 3.4 mPa·s, measured in situ by micro-rheology.

As shown in FIG. 14, it is demonstrated the validity of the tDASMP molecular rotor for measuring the intracellular viscosity of red blood cells whose main component is hemoglobin.

Conclusions

The inventors have first identified a molecular rotor, the DASPI (trans-4-[4-(dimethylamino)-styryl]-1 methylpyri-diniiodide), suitable for the study of hemoglobin and intra-cellular medium of red blood cells. For this purpose, the excitation emission spectra of the molecular rotor DASPI were measured in selected solutions: DMSO, ethylene gly-col, glycerol and hemoglobin. In all fluids, DASPI presented a fluorescence excitation peak around 480 nm and emission peak around 600 nm. As an important result, it has been shown that the excitation-emission spectrum of DASPI does not overlap the intrinsic fluorescent spectrum of hemoglobin in the ultraviolet. More, its emission spectrum is located in the range where the absorbance of hemoglobin is the lowest (~600 nm, FIG. 4), which allows it to be used at moderate concentrations.

Tested in simple solutions such as ethylene glycol/glyc-erol and glycerol/water solutions, the molecular rotor DASPI is sensitive to the local viscosity q, and exhibits a Förster-Hoffmann dependency in a range covering two decades, log $\varphi$=C+b log $\eta$, with $\varphi$ the LE-state quantum yield and b and C two solvent and dye-dependent param-eters. The exponent b, which is a measure of the efficiency of the molecular rotor in the solvent, was found to be around 0.7 in both solutions, which is close to the predicted theo-retical values, ⅔ or 0.6. The parameter C increases by about one and a half decade when the concentration of DASPI increases by two decades, which will allow to adjust the dye concentration to the sensitivity of the intensity reading device. The comparison between ethylene glycol/glycerol and glycerol/water solutions—one where the polarity effects are minimized, the other with variable polarity—confirms the previous result obtained by Haidekker and colleagues that there is no impact of variable polarity on obtaining a Förster-Hoffmann equation between quantum yield and vis-cosity.

The penetration of the molecular rotor DASPI was inves-tigated in healthy and rigidified red blood cells. Confocal microscopy experiments show that the molecular rotor spon-taneously penetrates into red blood cells in both cases. Given a depth of field around 600 nm, confocal microscopy unam-biguously separates the fluorescence response from the membrane and cytosol as soon as the focal plane is far enough from the membrane. The inventors could measure that the molecular rotor is uniformly distributed throughout the volume of RBCs, giving evidence that it is a suitable probe for characterizing their intracellular rheology.

These results demonstrated that existing molecular rotors were suitable to measure viscosity into physiologically relevant conditions, and this compared to current state of the art with micro-rheological methods. It has been shown that assays on red blood cell with an adequate molecular rotor were feasible and clinically relevant.

This test allows to quantify the correlation between the fluorescence response of molecular rotors able to penetrate cell membranes and rheological properties of the intracel-lular fluid, particularly to highlight the alteration of RBCs deformability and their dispersion and/or distribution in a blood sample.

Thus, based on this test, the inventors have found a new method for diagnosing a RBC related pathology associated with the presence of an alteration of the RBCs deformability in a subject, particular for diagnosing pathology selected from the group consisting of drepanocytosis, atherosclero-sis, diabetes, malaria and Alzheimer, more particularly for drepanocytosis.

BIBLIOGRAPHY

Banerjee R. et al. (1998) Clin. Hemorheol. Microcirc. 19, 21,
Barabino G. et al. (2010) Annu. Rev. Biomed. Eng. 12, 345,
Bessis M. et al. (1980) Blood Cells 6, 315
Du E. et al. (2015) PNAS 112, 1422
Guo Q. et al. (2014) J. Biomech. 47, 1767,
Habibi A. et al. (2015) La Revue de Médecine interne 36, 5S3,
Haidekker M. A. et al. (2010a) Springer Ser. Fluoresc. 8, 267
Haidekker M. A. et al. (2010b) J. Biol. Eng. 4, 11,
Kim, J. et al. (2015) J. Cell. Biotech. 1, 63,
Li, X. et al. (2017) PLoS comput. biol. 13, e1005426,
Nikitin S. Y. et al. (2015) Quantum Electronics 45, 776,
Piel, F. B. et al. (2017) N. Engl. J. Med. 376, 1561
Rabai M. et al. (2014) Biorheology 51, 159
Renoux C. et al. (2016) Clin. Hemorheol. Microcirc. 62, 173
Sosa J. M. et al. (2014) Clin. Hemorheol. Microcirc. 57, 275

The invention claimed is:

1. A method to detect in a test blood sample whether the red blood cells (RBCs) contained in the test blood sample present an alteration of their deformability, said method comprising the steps of:

a) mixing the test blood sample containing RBCs with a molecular rotor (MR) able to penetrate RBCs through their cell membranes to form a mixed test blood sample;

a') mixing a control blood sample known for exhibiting non alteration of RBC's deformability with a molecular rotor (MR) able to penetrate RBCs through their cell membranes to form a mixed control blood sample;

a") emitting an excitation light at 1) the mixed test blood sample to generate a test fluorescence signal and 2) the mixed control blood sample to generate a control fluorescence signal;

b) quantifying a level of the test fluorescence signal emitted by the molecular rotor in the mixed test blood sample and a level of the control fluorescence signal emitted by the molecular rotor in the mixed control blood sample and/or analysing a distribution of fluo-rescence level in RBCs among cells in the mixed test blood sample and in the mixed control blood sample; and c) comparing the quantified test fluorescence signal and the quantified control fluorescence signal and/or the distribution of fluorescence level in RBCs obtained in step b) for the mixed test blood sample with the distribution of fluorescence level in RBCs obtained for the mixed control blood sample, wherein an increase in the test fluorescence signal and/or a modification of the distribution of fluorescence level in RBCs for the mixed test blood sample compared to the control fluo-rescence signal and/or the distribution of fluorescence level in RBCs of the mixed control blood sample defines an alteration of the RBCs deformability present in the test blood sample, and wherein said molecular rotor (MR) is trans-4-[4-(Dimethylamino) styril]-1-methylpyridinium (tDASMP).

2. An in vitro method to identify whether a patient presents or to identify whether a patient is at risk to develop an RBC related pathology, said method comprising the steps of:

A) from a test blood sample containing RBCs obtained from the patient, detecting whether the RBCs present an alteration of their deformability by the method according to claim 1; and B) analysing detection results obtained in step A) for the test blood sample to determine whether the patient has an alteration of RBCs deformability, meaning said patient:

has an RBC related pathology, or is at risk of developing an RBC related pathology, wherein said RBC related pathology is selected from the group consisting of drepanocytosis, atherosclerosis, diabetes, malaria and Alzheimer's disease.

3. The method according to claim 2, wherein said RBC related pathology is drepanocytosis.

4. The method according to claim 1, wherein:

in step a) of the method of claim 1, the test blood sample is diluted in a solution of molecular rotor (MR);

in step a') of the method of claim 1, the control blood sample is diluted in a solution of molecular rotor (MR).

5. A method for diagnosing a RBC related pathology in a blood sample from a subject, wherein said RBC related pathology is selected from the group consisting of drepanocytosis, atherosclerosis, diabetes, malaria and Alzheimer's disease, the method comprising:

i) mixing a blood sample containing RBCs from the subject with molecular rotor (MR), which generates a fluorescence signal;

ii) emitting an excitation light at the mixture of the blood sample and molecular rotor (MR) to generate a fluorescence signal; and iii) determining by an optical method the following rheological properties of the RBCs: (a) distribution of rigidity; and/or (b) viscosity; and/or (c) deformability of the RBCs, by measuring a fluorescence intensity of an image of the blood sample, wherein said molecular rotor (MR) is the trans-4-[4-(Dimethylamino) styril]-1-methylpyridinium (tDASMP).

6. The method according to claim 5, wherein the optical method comprises utilizing a microscope coupled to a camera to image the blood sample.

7. The method according to claim 5, wherein said RBC related pathology is drepanocytosis.

8. The method according to claim 5, wherein:

in step i) the blood sample is diluted in a solution of molecular rotor (MR); and in step ii), a distribution of the RBCs fluorescence level is analysed and compared to a control sample.

9. A kit to identify whether a patient presents or is at risk to develop a RBC related pathology, wherein said RBC related pathology is selected from the group consisting of drepanocytosis, atherosclerosis, diabetes, malaria and Alzheimer's disease, said kit comprising trans-4-[4-(Dimethylamino)styril]-1-methylpyridinium (tDASMP) and red blood cells (RBCs) control exhibiting non alteration of their deformability and/or exhibiting alteration of their deformability characteristic of said RBC related pathology.

10. The kit according to claim 9, wherein said RBC related pathology is drepanocytosis.

\* \* \* \* \*